(12) United States Patent
Mor et al.

(10) Patent No.: US 8,710,179 B2
(45) Date of Patent: Apr. 29, 2014

(54) COMPOSITIONS AND METHODS FOR CONCENTRATING AND DEPLETING MICROORGANISMS

(75) Inventors: Amram Mor, Nesher (IL); Shahar Rotem, Kiryat-Tivon (IL); Yechezkel Kashi, Moshav HaYogev-D.N. Megiddo (IL); Nili Raz, Kiryat-Bialik (IL)

(73) Assignee: Technion Research & Development Foundation Limited, Haifa (IL)

( * ) Notice: Subject to any disclaimer, the term of this patent is extended or adjusted under 35 U.S.C. 154(b) by 391 days.

(21) Appl. No.: 12/448,214

(22) PCT Filed: Dec. 13, 2007

(86) PCT No.: PCT/IL2007/001544
§ 371 (c)(1),
(2), (4) Date: Feb. 3, 2010

(87) PCT Pub. No.: WO2008/072242
PCT Pub. Date: Jun. 19, 2008

(65) Prior Publication Data
US 2010/0143964 A1 Jun. 10, 2010

Related U.S. Application Data

(60) Provisional application No. 60/874,725, filed on Dec. 14, 2006.

(51) Int. Cl.
*A61K 38/00* (2006.01)
*C07K 2/00* (2006.01)
*C07K 4/00* (2006.01)
*C07K 5/00* (2006.01)
*C07K 7/00* (2006.01)

(52) U.S. Cl.
USPC ........................................................ 530/300

(58) Field of Classification Search
None
See application file for complete search history.

(56) References Cited

U.S. PATENT DOCUMENTS

2002/0146814 A1* 10/2002 Nilsson ..................... 435/287.1
2006/0074021 A1*  4/2006 Mor et al. ...................... 514/12

FOREIGN PATENT DOCUMENTS

WO   WO 00/23792      4/2000
WO   WO 2006/035431   4/2006

OTHER PUBLICATIONS

Gregory et al, Immobilization of *Escherichia coli* Cells by Use of the Antimicrobial Peptide Cecropin P1, Applied and Environmental Microbiology, Mar. 2005, p. 1130-1134.*
Gregory et al. "Immobilization of *Escherichia coli* Cells by Use of the Antimicrobial Peptide Cecropin P1", Applied and Environmental Microbiology, 71(3): 1130-1134, 2005. Abstract, p. 1133, Last § Before Acknowledgements.
Kulagina et al. "Antimicrobial Peptides for Detection of Bacteria in Biosensor Assays", Analytical Chemistry, 77(19): 6504-6508, 2005. Abstract, p. 6508, Last 2 §.
Stratmann et al. "Development of A Peptide-Mediated Capture PCR for Detection of *Myobacterium avium* Subsp. Paratuberculosis in Milk", Journal of Clinical Microbiology, 40(11): 4244-4250, 2002. Abstract.
International Search Report Dated Mar. 31, 2008 From the International Searching Authority Re. Application No. PCT/IL2007/001544.
Written Opinion Dated Mar. 31, 2008 From the International Searching Authority Re. Application No. PCT/IL2007/001544.
Office Action Dated Jul. 3, 2011 From the Israel Patent Office Re. Application No. 199297 and Its Translation Into English.
Communication Pursuant to Article 94(3) EPC Dated Jun. 10, 2013 From the European Patent Office Re. Application No. 07849570.2.
Requisition by the Examiner Dated Jan. 29, 2014 From the Canadian Intellectual Property Office Re. Application No. 2,672,161.

* cited by examiner

*Primary Examiner* — Cecilia J Tsang
*Assistant Examiner* — Sergio Coffa

(57) ABSTRACT

Methods for concentrating microorganisms in a liquid sample or depleting microorganisms therefrom, utilizing polymeric compounds having affinity to microbial cells that are composed of a plurality of positively charged amino acid residues and two or more hydrophobic moieties are disclosed. Also disclosed are devices for concentrating and methods for detection and identification microorganisms in a liquid sample.

39 Claims, 10 Drawing Sheets

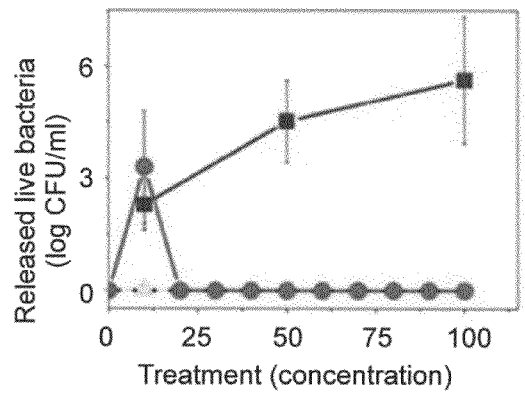
Fig. 3
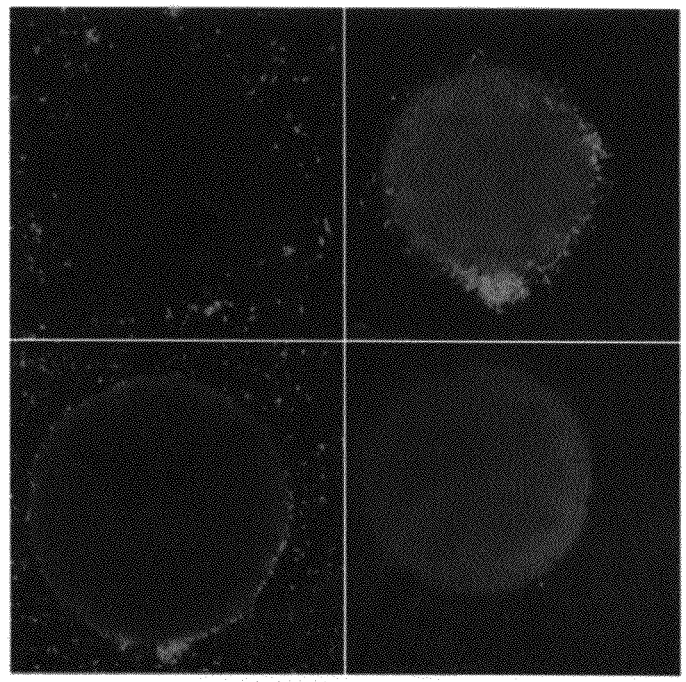
Fig. 4a   Fig. 4c
Fig. 4b   Fig. 4d

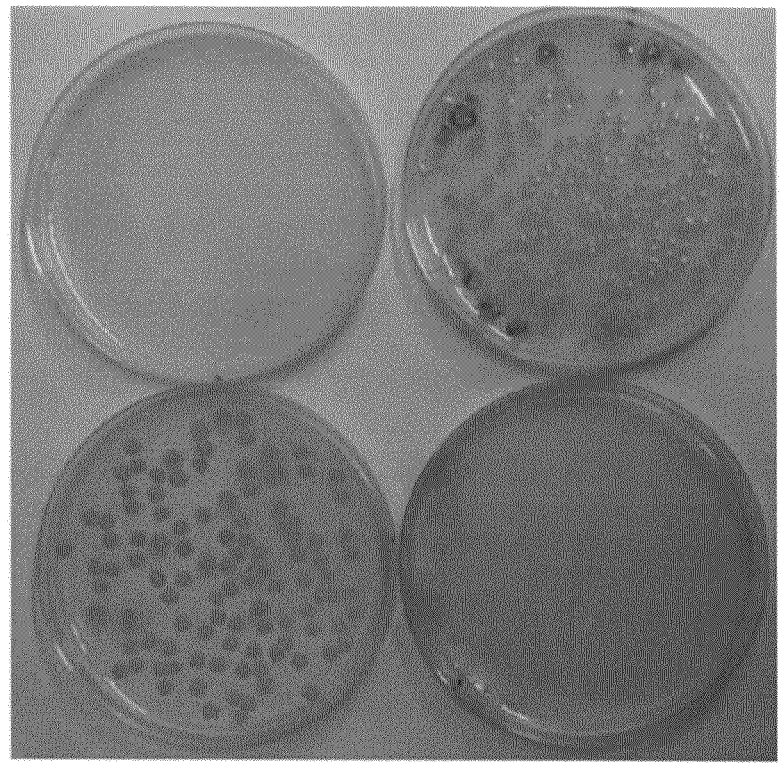
Fig. 6a1  Fig. 6b1
Fig. 6a2  Fig. 6b2

COMPOSITIONS AND METHODS FOR CONCENTRATING AND DEPLETING MICROORGANISMS

RELATED APPLICATIONS

This Application is a National Phase of PCT Patent Application No. PCT/IL2007/001544 having International filing date of Dec. 13, 2007, which claims the benefit of U.S. Provisional Patent Application No. 60/874,725 filed on Dec. 14, 2006. The contents of the above Applications are all incorporated herein by reference.

FIELD AND BACKGROUND OF THE INVENTION

The present invention, in some embodiments thereof, relates to microbiology and, more particularly, but not exclusively, to bacterial sample concentration and depletion techniques.

Microbial contamination of potable water can put water consumers at risk even at low concentrations and short exposure time periods, and therefore rapid, accurate and sensitive pathogen detection techniques are in ever-present demand. Similarly, rapid detection and unambiguous identification of pathogens is crucial in life-threatening medical situations. A key step in most contamination detection methods for pathogenic microorganisms in liquid media is concentration, which is necessary due to the typically low ambient densities of pathogens in the media which are usually lower than the limit of detection.

The emergence of new rapid detection and analysis of microorganisms is closely linked to the development of new concentration methods. For example, immunological or PCR based methods are used after an incubation step because of a minimal detection limit, which hampers the process of rapid detection. In research there has been an emphasis on the development of high throughput screening (HTS) for microbial cell-identification assays using, for example, real-time PCR, microarrays, immunofluorescent methods and combinations thereof. These research studies require a process to lyse bacterial cells, purify and label nucleic acids, and detect organism signatures using microarrays and other HTS techniques. Also, work has been conducted to automate separation of DNA and whole cells from soils, sediments, food, and water. However, these rapid procedures require extensive and time-consuming cell-sample preparations since a high throughput assay usually only reflects the endpoint detector step and not the entire process of sample concentration and preparation which is needed for optimal detection.

One of the most widely used techniques for concentration of microorganisms in liquid media utilizes a size-cutoff membrane filters (MF) through which the liquid media is filtered and the pathogen's cells are stopped by the membrane and thus concentrated. Such a technique is usually the method of choice for the determination of total coliforms, a commonly used indicator of fecal contamination in water. While the MF method is simple and yields definitive results, factors such as elevated turbidity, ambient particles and sediments, resulting in membrane filter blockage, and other filter-type related factors such as inhibition of microbial growth at grid lines, abnormal spreading of colonies, non wetting areas, brittleness, severe wrinkling and decreased recovery, may severely influence the viability, accuracy and sensitivity of the procedure and lead to false and ill-reproducible results. Moreover, the need to concentrate large volumes of the tested media in order to compensate for spatial and temporal variations in pathogen occurrence, increases the probability of membrane filter blockage.

Alternatively, microorganisms can be concentrated and separated from their constituent matrix components in a number of ways. For example, whole bacterial cells have been isolated from food using reagents such as hydroxyapatite. Antibodies coupled to magnetic beads were used to separate specific organisms from human fluids, food, and water, and are widely used in many different applications. Novel methods for semi-specific capture of microorganisms using cell-surface derived lectins and carbohydrates have also been proposed.

Peptides and peptide-mimetic compounds have been investigated for use for broad-spectrum and/or specific binding of microorganisms. Specific capture of mycobacterium in milk was attempted using peptide conjugation to a polymer [1]. Furthermore, antimicrobial peptides linked to surfaces were used for killing [2], immobilization [3] and detection [4] of bacteria.

WO2006/035431 teaches a novel class of antimicrobial polymeric agents which are designed to specifically bind and kill the cell via a two-step mechanism involving an initial high affinity interaction with the microbial external membranes followed by internalization which eventually kills the cell. WO2006/035431 further discloses pharmaceutical compositions and food additives containing these agents as well as methods of treating medical conditions associated with pathological microorganisms. Hence, all the applications described by WO2006/035431 are related to cell killing.

SUMMARY OF THE INVENTION

The present invention relates to the use of matrix-bound polymeric compounds, or polymers, which are capable of binding to the membrane of microorganisms with relatively high affinity, and according to some embodiments of the present invention, to the use of such compositions in concentration and depletion of microorganisms from a liquid aqueous media, which is an essential step in the detection and identification of microorganisms and many medical, analytical, diagnostic and research applications.

The present inventors have found that previously described bactericidal polymers, can be used, when bound to an insoluble matrix, to efficiently bind the microorganism while retaining its viability. This finding can be harnessed towards various microbial concentration and depletion applications.

Without being bound to theory, its suggested that AMPs and previously described antimicrobial polymers (see e.g., U.S. Patent Application Nos. 2006/0074021 and 2007/0032428, WO 2006/035431 and U.S. Provisional Patent Application Nos. 60/924,087 and 60/924,088, all of which are incorporated as if fully set forth herein) have a mode of action which follows a two-step mechanism involving an initial high affinity interaction with bacterial external membrane(s) followed with an internalization process that eventually leads to cell death. By linking these antimicrobial polymers to an inert solid support, the attribute of the high binding affinity of the polymers to microorganisms' membrane was exploited while substantially eliminating the cell-killing effect. In the embodiments presented hereinbelow various polymer derivatives have been produced and covalently linked to a solid support matrix such as, for example, a polystyrene-based resin via, for example, the C-terminus thereof. These polymer-matrix constructs were shown to retain the binding properties to superficial components of microbial cell membranes and hence capture the cells, while maintaining the viability of the captured cells. These polymer-matrix constructs were used to bind, and thus concentrate or deplete microorganisms in a variety of aqueous solutions such as contaminated water, bodily fluids and the likes, which is a crucial step in the detection and identification of microorganisms.

Hence, according to an aspect of some embodiments of the present invention there is provided a method of concentrating microorganisms in an aqueous solution, effected by contacting the solution with a water-insoluble matrix having a polymer capable of binding the microorganism covalently attached thereto, the polymer includes a plurality of residues, wherein the plurality of residues includes a plurality of amino acid residues and at least two hydrophobic moiety residues, whereas at least one of the hydrophobic moiety residues is being covalently linked to at least two amino acid residues in the plurality of amino acid residues via an amine group of one amino acid residue and via a carboxyl of the other amino acid residue in the at least two amino acid residues, the polymer being selected from the group consisting of a linear polymer and a cyclic polymer, thereby binding the microorganisms to the polymer on the matrix and concentrating the microorganisms in the aqueous solution.

According to another aspect of some embodiments of the present invention there is provided a method of depleting microorganisms from an aqueous solution, the method is effected by:

(a) contacting the solution with a water-insoluble matrix having a polymer as described herein capable of binding the microorganism, covalently attached thereto, thereby binding the microorganisms to the polymer on the matrix; and subsequently (b) collecting the solution depleted from the microorganisms.

According to yet another aspect of some embodiments of the present invention there is provided a device for concentrating microorganisms which includes one or more casings and a water-insoluble matrix embedded therein, the water insoluble matrix having a polymer as described herein capable of binding the microorganism covalently attached thereto, wherein the matrix is configured to allow an aqueous solution which includes the microorganism to flow through, thereby binding the microorganisms to the polymer on the matrix.

According to still another aspect of some embodiments of the present invention there is provided a method for detection and identification of microorganisms in an aqueous solution which is effected by:

(a) contacting the solution with a water-insoluble matrix having a polymer as described herein capable of binding the microorganism covalently attached thereto, thereby binding the microorganisms to the polymer on the matrix; and (b) identifying the microorganism bound to the matrix.

According to an aspect of some embodiments of the present invention there is provided a sterile composition which includes a water-insoluble matrix having a polymer as described herein capable of binding the microorganism covalently attached thereto.

According to an aspect of some embodiments of the present invention there is provided a composition which includes a water-insoluble matrix having a polymer as described herein capable of binding the microorganism covalently attached thereto, and microorganisms bound to the polymer.

According to some embodiments of the invention, the plurality of amino acid residues includes at least one positively charged amino acid residue.

According to some embodiments of the invention, the hydrophobic moiety residue is linked to at least one of the amino acid residues via a peptide bond.

According to some embodiments of the invention, the hydrophobic moiety residue is linked to each of the two amino acid residues via a peptide bond.

According to some embodiments of the invention, the hydrophobic moiety has a carboxylic group at one end thereof and an amine group at the other end thereof.

According to some embodiments of the invention, the plurality of amino acid residues includes from 2 to 50 amino acid residues.

According to some embodiments of the invention, the positively charged amino acid residue is selected from the group consisting of a histidine residue, a lysine residue, an ornithine residue and an arginine residue.

According to some embodiments of the invention, the polymer includes from 2 to 50 hydrophobic moiety residues.

According to some embodiments of the invention, the hydrophobic moiety residue includes at least one fatty acid residue.

According to some embodiments of the invention, the hydrophobic moiety is an ω-amino-fatty acid residue.

According to some embodiments of the invention, the hydrophobic moiety is selected from the group consisting of 4-amino-butyric acid, 8-amino-caprylic acid and 12-amino-lauric acid.

According to some embodiments of the invention, the plurality of amino acid residues substantially consists of positively charged amino acid residues.

According to some embodiments of the invention, the positively charged amino acid residues are selected from the group consisting of lysine residues, histidine residues, ornithine residues, arginine residues and combinations thereof.

According to some embodiments of the invention, the plurality of amino acid residues substantially consists of positively charged amino acid residues.

According to some embodiments of the invention, the positively charged amino acid residues are lysine residues.

According to some embodiments of the invention, the polymer is having the general Formulae I or II:

$$X-W_0-[A_1-Z_1-D_1]-W_1-[A_2-Z_2-D_2]-W_2-\ldots[A_n-Z_n-D_n]-W_n-Y \quad \text{Formula I}$$

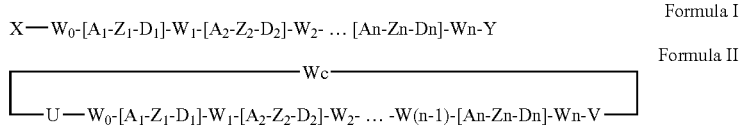

Formula II wherein:

n is an integer from 2 to 50;

$A_1, A_2, \ldots, A_n$ are each independently an amino acid residue;

$D_1, D_2, \ldots, D_n$ are each independently a hydrophobic moiety residue or absent, provided that at least one of the $D_1, D_2, \ldots, D_n$ is the hydrophobic moiety residue;

$Z_1, Z_2, \ldots, Z_n$ and $W_0, W_1, W_2, \ldots, W_n$ are each independently a linking moiety linking an amino acid residue and a hydrophobic moiety residue, or absent;

X and Y are each independently hydrogen, an amine, an amino acid residue, a hydrophobic moiety residue, has the general Formula I or absent;

$W_0$ is a linking moiety linking one of the $A_1$, $Z_1$ and $D_1$ to U, or absent;

Wn is a linking moiety linking one of the An, Zn and Dn to V, or absent;

U is selected from the group consisting of a first functional group, an amino acid residue having the first functional group, a hydrophobic moiety residue having the first functional group, and a linking moiety having the first functional group or absent;

V is selected from the group consisting of a second functional group, an amino acid residue having the second functional group, a hydrophobic moiety residue having the second functional group, and a linking moiety having the second functional group or absent; and Wc is a cyclizing moiety.

According to some embodiments of the invention, X is a hydrophobic moiety residue.

According to some embodiments of the invention, Y is a hydrophobic moiety residue.

According to some embodiments of the invention, at least one of $W_0, W_1, W_2, \ldots W_n$ and $Z_1, Z_2, \ldots Z_n$ is a peptide bond.

According to some embodiments of the invention, Wc is a peptide bond.

According to some embodiments of the invention, each of $W_0, W_1, W_2, \ldots W_n$ and $Z_1, Z_2, \ldots Z_n$ is a peptide bond.

According to some embodiments of the invention, at least one of $D_1, D_2, \ldots,$ Dn is a ω-amino-fatty acid residue.

According to some embodiments of the invention, at least one of the hydrophobic moieties includes at least one hydrocarbon chain.

According to some embodiments of the invention, at least one of the hydrophobic moieties includes at least one fatty acid residue.

According to some embodiments of the invention, each of $A_1, A_2, \ldots,$ An is a lysine residue.

According to some embodiments of the invention, each of the $D_1, D_2, \ldots,$ Dn is a 12-amino-lauric acid.

According to some embodiments of the invention, n is an integer from 5 to 7.

According to some embodiments of the invention, X is a dodecanoic acid residue and Y is an amine.

According to some embodiments of the invention, the method of concentrating further includes collecting the microorganisms following binding thereof.

According to some embodiments of the invention, the binding is effected in vitro or ex-vivo.

According to some embodiments of the invention, the contacting is effected under stationary incubation conditions and/or under continuous flow conditions.

According to some embodiments of the invention, the methods further include, subsequent to contacting the solution with the matrix, releasing the microorganisms from the matrix.

According to some embodiments of the invention, the methods further include, prior to identifying the microorganisms, isolating the microorganisms from the matrix.

According to some embodiments of the invention, the matrix is selected suitable for repeated use.

According to some embodiments of the invention, the polymer is covalently attached to the matrix via a C-terminus of the polymer.

According to some embodiments of the invention, the binding is effected while maintaining viability of the microorganisms.

According to some embodiments of the invention, the polymer is having the formula:

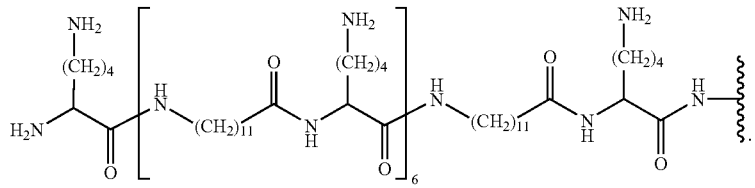

According to some embodiments of the invention, detection and identification of microorganisms is quantitative.

According to some embodiments of the invention, the aqueous solution is selected from the group consisting of potable water, reservoir water, natural source water, swimming pool water, hot-tub water, fountain water, sewage, wastewater, spent water, irrigation water, a liquid consumer product, a liquid food product, an biological or biochemical assay solution, a bodily fluid, a blood sample, a culture medium, a urine sample, a spinal fluid sample, a saliva sample, tears and an amniotic fluid sample.

According to some embodiments of the invention, the matrix is selected from the group consisting of a polymeric matrix, a glass matrix, a metal matrix, a ceramic matrix, an inorganic matrix and any combination thereof.

According to some embodiments of the invention, the form of the matrix is selected from the group consisting of a flat surface, a fiber, a tube, a bead, a sphere, a mesh, a net, a web, a grid, a lattice, a plexus, a screen, a filter and any combination thereof.

According to some embodiments of the invention, the identifying of the microorganism is effected by a technique selected from the group consisting of a visual identification, a DNA amplification (PCR), a morphological identification, a biochemical identification, a microbiological identification and an immunological identification.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings, images and plots. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-D presents the results of the bacterial capturing assays using $K(NC_{12}K)_7NH_2$ as an exemplary bead-bound polymer according to some embodiments of the present invention, wherein FIG. 2A is a comparative bar-plot, showing the CFU count of the un-captured $E.$ $coli$ cells found in the filtrates after 30 minutes incubation at the specified concentrations ($10^4$-$10^8$ CFU/ml) with 1.8 mg of Boc-protected (grey) and unprotected (white) $K(NC_{12}K)_7NH_2$ polymer, whereas the actual count was performed by plating the filtrates on LB agar for enumeration, FIG. 2B is a comparative plot showing the time dependence of $E.$ $coli$ capture as assessed by CFU count determined for filtrates after incubation at the specified time periods in the presence of 1.8 mg of deprotected (red rectangles) and Boc-protected (green circles) $K(NC_{12}K)_7NH_2$-loaded beads, and $K_{15}NH_2$-loaded beads (blue triangles) were used as control, whereas the insert shows a low concentration experiment comparing $K_{15}NH_2$-loaded beads (blue triangles) and the bare resin as control (green circles); FIG. 2C is a bar-plot showing the binding capacity of $E.$ $coli$ ($1\times10^6$ CFU/ml/cycle) to 1.8 mg of unprotected $K(NC_{12}K)_7NH_2$ polymer as determined by repeated incubation/filtration cycles (depletion assays), wherein after each cycle, the filtrate was plated on LB agar for enumeration, and "PR" represents a one-cycle control experiment performed with a 1.8 mg Boc-protected polymer, and FIG. 2D is a comparative bar-plot, showing the bacterial binding specificity of the exemplary $K(NC_{12}K)_7NH_2$ polymer versus a variety of bacterial strains as determined for filtrates after 30 minutes incubation in the presence of 1.8 mg of the Boc-protected (white) and unprotected beads-bound polymer with $1\times10^6$ CFU/ml of each of $E.$ $coli$ (E.c.), $V.$ $cholerae$ (V.c.), $E.$ $faecalis$ (E.f.) and $S.$ $aureus$ (S.a.);

FIG. 3 is a comparative plot showing the viability of bacteria after elution from $K(NC_{12}K)_7NH_2$-loaded resin beads using lipopolysaccharide (X-axis denotes the concentration in ng/ml, and data marked in green rectangles); 10% ammonium sulphate:ethanol solution in water (concentration in % ethanol v/v and data marked in pink circles); ethanol in water (concentration in % ethanol v/v and data marked in yellow triangles);

FIGS. 4A-D presents a series of fluorescence confocal microscopy images of GFP-expressing $E.$ $coli$, wherein the bacteria was detected in the surrounding medium after failing to bind to the exemplary Boc-protected $K(NC_{12}K)_7NH_2$-loaded resin beads control sample (FIG. 4A), but was captured by the unprotected $K(NC_{12}K)_7NH_2$-loaded resin beads (FIG. 4B), indicating that bacterial adhesion occurs during the incubation and prior to filtration, and further showing that the bacteria remained attached to the unprotected polymer sample after the filtration step (FIG. 4C), which is consistent with high binding affinity, and that 5 minutes treatment with 70% ethanol resulted in dissociation of the polymer-captured bacteria (FIG. 4D) suggesting that the beads-bound polymers can be recycled readily;

FIGS. 5A-D presents a series of fluorescence confocal microscopy images of $K(NC_{12}K)_7NH_2$-captured GFP-expressing $E.$ $coli$ after treatment with propidium iodide, wherein the green and red colors indicate live and dead bacteria, respectively (FIG. 5A is a low magnification image and FIGS. 5B-D are zoomed images), whereas FIG. 5C is an image recorded before treatment with the antimicrobial peptide dermaseptin and FIG. 5D is an image recorded after treatment with dermaseptin;

FIGS. 6A1-B2 presents a series of images of LB-agar plates, showing the viability of the captured $E.$ $coli$ cells ($1\times10^6$ CFU/ml) which were incubated for 30 minutes with deprotected (FIGS. 6A1 and 6A2) and Boc-protected (FIGS. 6B1 and 6B2) $K(NC_{12}K)_7NH_2$-loaded resin beads, wherein FIGS. 6A1 and 6B1 show the plates of the plated filtrates and FIGS. 6A2 and 6B2 show the plates of filtered and plated beads;

DESCRIPTION OF SPECIFIC EMBODIMENTS OF THE INVENTION

Figure 1:
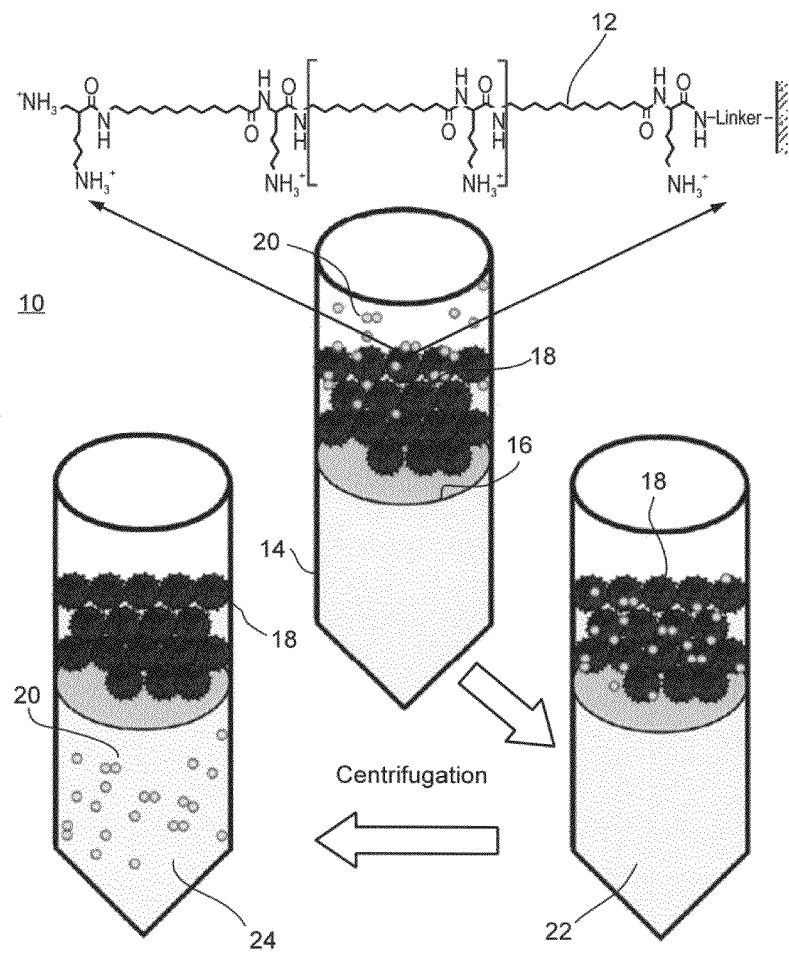
FIG. 1 is a simplified illustration of an exemplary microorganism-capturing device according to some embodiments of the present invention, composed of an exemplary polymer which is linked to particles of a water-insoluble matrix (such as resin beads), and a centrifuge filter-tube is packed with such polymer-loaded resin beads (large dark spheres) which are incubated with a sample of microorganism cells (small light spheres), showing the capturing and concentration of the microorganism by the polymer-loaded resin beads after incubation and centrifugation (bottom-right tube), and the subsequent release of the microorganism from the polymer-loaded resin beads (bottom-left tube)

The present invention, in some embodiments thereof, relates to microbiology and, more particularly, but not exclusively, to microbial sample concentration or depletion, detection and identification techniques, which offer a solution for many of the major drawbacks of presently known methods for concentrating microorganisms for the purpose of detection and identification thereof. The present invention further offers an improved method for rapid and effective concentration or depletion of microorganisms from liquid samples of any volume and particle content, and particularly when the requirement is a non-destructive method.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As mentioned hereinabove, antimicrobial polymers comprising a plurality of positively charged amino acid residues and hydrophobic moiety residues, and substantially composed of tandem repeats of capryl- and/or lauryl-lysines conjugates, which were designed to possess high affinity interaction with microbial external membrane(s), were investigated as potential matrix-bound microbial binding agents.

While reducing the present invention to practice, the inventors have designed a heptameric polymer, composed of a tandem repeat of seven 12-aminolauroyl-lysine to subunits whose N-terminus was capped with an additional lysine residue and its C-terminus was covalently linked to a polystyrene-based resin. While testing this resin-bound polymer for cell binding, it was found that the cell-killing attribute was substantially reduced, making this polymer-resin construct an ideal tool for capturing viable (live) microorganisms.

Without being bound by any particular theory, it was assumed that the polymer-resin construct restrains the ability of the resin-linked polymer to interact with internal cellular components without altering its binding properties to superficial membranal components of microbial cells. These findings and hypothesis lead to the designed of an effective method, devices and systems for concentrating or depleting microorganisms from aqueous solutions, as presented hereinbelow.

Method of Concentrating

Hence, according to one aspect of the present invention, there is provided a method of concentrating microorganisms in an aqueous solution which is effected by contacting (incubating) the aqueous solution containing the microorganisms with a water-insoluble matrix having a polymer capable of binding microorganisms, as described in details hereinbelow, covalently attached thereto; and thereby binding the microorganisms to the polymer on the matrix and concentrating the microorganisms in the aqueous solution.

As discussed hereinabove and demonstrated in the Examples section that follows, the polymers according to some embodiments of the present invention are capable of binding to the membrane of microorganisms. During the time period which the aqueous solution is in contact, or incubated with the matrix, the microorganisms interact with the polymer which is attached to (immobilized on) the matrix, and bind thereto. Hence, by collecting the matrix after the incubation period, a concentrated sample of the microorganism is obtained. According to some embodiments of the present invention, the microorganisms can be retrieved from the matrix by various means, as detailed hereinbelow. Alternatively, the matrix-bound microorganism can be used directly for various purposes such as detection and identification thereof.

Hence, according to some embodiments of the present invention, the method for concentrating microorganisms further includes collecting the matrix with the microorganisms following the incubation and binding process, and may further include releasing the microorganisms from the matrix, following protocols presented hereinbelow.

The term "concentrating" as used herein, refers to the action of raising the concentration of microorganism in the solution, which is originally lower that the detectable level of a given detection technique, to a level which is sufficient for detection by the technique. The detection level of microorganisms is typically measured in CFU, or colony-forming units, which was used to quantify inoculum in the experimental tests presented in Examples which follows hereinbelow.

Colony-forming unit (CFU) is a measure of viable microbial numbers, rather than counting all cells, dead and living. CFU is determined by spreading or pouring a sample containing a microorganism on a surface of an agar plate, a process which is commonly referred to as "plating", and leaving the plate to incubate until visible colonies of the microorganism are formed, and then the number of colonies is counted.

Method of Depleting

According to another aspect of the present invention there is provided a method of depleting microorganisms from an aqueous solution, which is effected by:

(a) contacting the solution with a water-insoluble matrix having a polymer, capable of binding microorganisms, as described in details hereinbelow, covalently attached thereto, thereby binding the microorganisms to the polymer on the matrix; and subsequently (b) collecting the solution depleted from the microorganisms.

As in the method for concentrating a aqueous solution, the microorganisms are allowed to bind to the matrix-bound polymer, however, in this method the aqueous solution is the part which is collected for any purpose. This method is using the matrix-polymer construct to remove, or "filter" the microorganism from the aqueous solution, and the "filtrate" is collected.

As used herein, the term "depleting", refers to the action of lowering the concentration of microorganism in the solution, which is originally high enough for detection by a given detection technique, to a level which is lower than the detectable level of detection by the technique.

Alternatively, the depletion of microorganism, according to some embodiments of the present invention, is performed so as to lower the concentration of microorganism in a solution from unacceptable levels to acceptable contamination levels according to standards determined for any given use of the aqueous solution.

Microorganisms

The methods as described herein can be used to concentrate or deplete microorganism which are found in aqueous solutions, including, but not limited to pathogenic microorganism.

Herein throughout, the phrase "microorganism" is used to describe microscopic unicellular organism which may belong to any family of organisms such as, but not limited to prokaryotic organisms, eubacterium, proteobacterium, archaebacterium, eukaryotic organisms, yeast, fungi, algae, protists, protozoan, and other parasites, as exemplified hereinbelow.

Non-limiting examples of prokaryotic bacteria phyla include acidobacteria, actinobacteria, aquificae, bacteroidetes, chlamydiae, chlorobi, chloroflexi, chrysiogenetes, cyanobacteria, deferribacteres, deinococcus-thermus, dictyoglomi, fibrobacteres, firmicutes, fusobacteria, gemmatimonadetes, nitrospirae, planctomycetes, proteobacteria, spirochaetes, thermodesulfobacteria, thermomicrobia, thermotogae and verrucomicrobia.

Non-limiting examples of archaebacterium phyla include crenarchaeota, euryarchaeota, korarchaeota, nanoarchaeota and ARMAN (Archaeal Richmond Mine Acidophilic Nanoorganisms).

Non-limiting examples of proteobacteria include Alpha proteobacteria such as *Caulobacterales* (*Caulobacter*), *Parvularculales, Rhizobiales* (*rhizobia*), *Rhodobacterales, Rhodospirillales* (*Acetobacter*), *Rickettsiales* (*Rickettsia*) and *Sphingomonadales* (*Sphingomonas*); Beta proteobacteria such as *Burkholderiales* (*Bordetella*), *Hydrogenophilales, Methylophilales, Neisseriales* (*Neisseria*), *Nitrosomonadales, Rhodocyclales* and *Procabacteriales*; Gamma proteobacteria such as *Acidithiobacillales, Aeromonadales* (*Aeromonas*), *Alteromonadales* (*Pseudoalteromonas*), *Cardiobacteriales, Chromatiales* (purple sulfur bacteria), *Enterobacteriales* (*Escherichia*), *Legionellales* (*Legionella, Methylococcales, Oceanospirillales, Pasteurellales* (*Haemophilus*), *Pseudomonadales* (*Pseudomonas*), *Thiotrichales* (*Thiomargarita*), *Vibrionales* (*Vibrio*) and *Xanthomonadales* (*Xanthomonas*); Delta proteobacteria such as *Bdellovibrionales* (*Bdellovibrio*), *Desulfobacterales, Desulfovibrionales, Desulfurellales, Desulfarcales, Desulfuromonadales* (*Geobacter*), *Myxococcales, Myxobacteria* and *Syntrophobacterales*; and Epsilon proteobacteria such as *Campylobacterales* (*Helicobacter*) and *Nautiliales*.

Herein throughout, the phrase "pathogenic microorganism" is used to describe any microorganism which can cause a disease or disorder in a higher organism, such as mammals in general and a human in particular.

Non-limiting examples of pathogenic microorganism are *Escherichia, Helicobacter, Plasmodium falciparum* and related malaria-causing protozoan parasites, *Acanthamoeba* and other free-living amoebae, *Aeromonas hydrophila, Anisakis* and related worms, *Ascaris lumbricoides, Bacillus cereus, Campylobacter jejuni, Clostridium botulinum, Clostridium perfringens, Cryptosporidium parvum, Cyclospora cayetanensis, Diphyllobothrium, Entamoeba histolytica, Eustrongylides, Giardia lamblia, Listeria monocytogenes, Nanophyetus, Plesiomonas shigelloides, Salmonella, Shigella, Staphylococcus aureus, Streptococcus, Trichuris trichiura, Vibrio cholerae, Vibrio parahaemolyticus, Vibrio vulnificus* and other vibrios, *Yersinia enterocolitica* and *Yersinia pseudotuberculosis*.

Polymer Capable of Binding Microorganisms

A polymer capable of binding microorganisms, according to embodiments of the present embodiments, comprises four or more monomers, also referred to herein interchangeably as residues, which include two or more amino acid residues and two or more hydrophobic moiety residues, as these terms are defined hereinbelow, whereas at least one of the hydrophobic moiety residues is covalently linked to at least two amino acid residues via an amine group of one amino acid and via a carboxyl group of the other amino acid residue. The polymer can be a linear polymer or a cyclic polymer, as these terms are defined hereinbelow. Therefore, the polymers described herein each is comprised of a linear or cyclic chain made of a sequence of amino acid residues, interrupted and terminated by two or more hydrophobic moiety residues.

As used herein throughout the term "amino acid" or "amino acids" is understood to include the 20 genetically coded amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids and other non-naturally occurring amino acids.

Tables 1 and 2 below list the genetically encoded amino acids (Table 1) and non-limiting examples of non-conventional/modified amino acids (Table 2) which can be used with the present invention.

TABLE 1

| Amino acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| aminoisobutyric acid | Aib | L-N-methylaspartic acid | Nmasp |
| aminonorbornyl-carboxylate | Norb | L-N-methylcysteine | Nmcys |
| Cyclohexylalanine | Chexa | L-N-methylglutamine | Nmgln |
| Cyclopentylalanine | Cpen | L-N-methylglutamic acid | Nmglu |
| D-alanine | Dal | L-N-methylhistidine | Nmhis |
| D-arginine | Darg | L-N-methylisoleucine | Nmile |
| D-aspartic acid | Dasp | L-N-methylleucine | Nmleu |
| D-cysteine | Dcys | L-N-methyllysine | Nmlys |
| D-glutamine | Dgln | L-N-methylmethionine | Nmmet |
| D-glutamic acid | Dglu | L-N-methylnorleucine | Nmnle |
| D-histidine | Dhis | L-N-methylnorvaline | Nmnva |
| D-isoleucine | Dile | L-N-methylornithine | Nmorn |
| D-leucine | Dleu | L-N-methylphenylalanine | Nmphe |
| D-lysine | Dlys | L-N-methylproline | Nmpro |
| D-methionine | Dmet | L-N-methylserine | Nmser |
| D/L-ornithine | D/Lorn | L-N-methylthreonine | Nmthr |
| D-phenylalanine | Dphe | L-N-methyltryptophan | Nmtrp |
| D-proline | Dpro | L-N-methyltyrosine | Nmtyr |
| D-serine | Dser | L-N-methylvaline | Nmval |
| D-threonine | Dthr | L-N-methylethylglycine | Nmetg |
| D-tryptophan | Dtrp | L-N-methyl-t-butylglycine | Nmtbug |
| D-tyrosine | Dtyr | L-norleucine | Nle |
| D-valine | Dval | L-norvaline | Nva |
| D-α-methylalanine | Dmala | α-methyl-aminoisobutyrate | Maib |
| D-α-methylarginine | Dmarg | α-methyl-γ-aminobutyrate | Mgabu |
| D-α-methylasparagine | Dmasn | α-methylcyclohexylalanine | Mchexa |
| D-α-methylaspartate | Dmasp | α-methylcyclopentylalanine | Mcpen |
| D-α-methylcysteine | Dmcys | α-methyl-α-napthylalanine | Manap |
| D-α-methylglutamine | Dmgln | α-methylpenicillamine | Mpen |
| D-α-methylhistidine | Dmhis | N-(4-aminobutyl)glycine | Nglu |
| D-α-methylisoleucine | Dmile | N-(2-aminoethyl)glycine | Naeg |
| D-α-methylleucine | Dmleu | N-(3-aminopropyl)glycine | Norn |
| D-α-methyllysine | Dmlys | N-amino-α-methylbutyrate | Nmaabu |
| D-α-methylmethionine | Dmmet | α-napthylalanine | Anap |
| D-α-methylornithine | Dmorn | N-benzylglycine | Nphe |
| D-α-methylphenylalanine | Dmphe | N-(2-carbamylethyl)glycine | Ngln |
| D-α-methylproline | Dmpro | N-(carbamylmethyl)glycine | Nasn |
| D-α-methylserine | Dmser | N-(2-carboxyethyl)glycine | Nglu |
| D-α-methylthreonine | Dmthr | N-(carboxymethyl)glycine | Nasp |
| D-α-methyltryptophan | Dmtrp | N-cyclobutylglycine | Ncbut |
| D-α-methyltyrosine | Dmty | N-cycloheptylglycine | Nchep |
| D-α-methylvaline | Dmval | N-cyclohexylglycine | Nchex |
| D-α-methylalnine | Dnmala | N-cyclodecylglycine | Ncdec |
| D-α-methylarginine | Dnmarg | N-cyclododeclglycine | Ncdod |
| D-α-methylasparagine | Dnmasn | N-cyclooctylglycine | Ncoct |
| D-α-methylasparatate | Dnmasp | N-cyclopropylglycine | Ncpro |
| D-α-methylcysteine | Dnmcys | N-cycloundecylglycine | Ncund |
| D-N-methylleucine | Dnmleu | N-(2,2-diphenylethyl)glycine | Nbhm |
| D-N-methyllysine | Dnmlys | N-(3,3-diphenylpropyl)glycine | Nbhe |
| N-methylcyclohexylalanine | Nmchexa | N-(3-indolylethyl)glycine | Nhtrp |
| D-N-methylornithine | Dnmorn | N-methyl-γ-aminobutyrate | Nmgabu |
| N-methylglycine | Nala | D-N-methylmethionine | Dnmmet |

TABLE 2-continued

| Non-conventional amino acid | Code | Non-conventional amino acid | Code |
| --- | --- | --- | --- |
| N-methylaminoisobutyrate | Nmaib | N-methylcyclopentylalanine | Nmcpen |
| N-(1-methylpropyl)glycine | Nile | D-N-methylphenylalanine | Dnmphe |
| N-(2-methylpropyl)glycine | Nile | D-N-methylproline | Dnmpro |
| N-(2-methylpropyl)glycine | Nleu | D-N-methylserine | Dnmser |
| D-N-methyltryptophan | Dnmtrp | D-N-methylserine | Dnmser |
| D-N-methyltyrosine | Dnmtyr | D-N-methylthreonine | Dnmthr |
| D-N-methylvaline | Dnmval | N-(1-methylethyl)glycine | Nva |
| γ-aminobutyric acid | Gabu | N-methyla-napthylalanine | Nmanap |
| L-t-butylglycine | Tbug | N-methylpenicillamine | Nmpen |
| L-ethylglycine | Etg | N-(p-hydroxyphenyl)glycine | Nhtyr |
| L-homophenylalanine | Hphe | N-(thiomethyl)glycine | Ncys |
| L-α-methylarginine | Marg | penicillamine | Pen |
| L-α-methylaspartate | Masp | L-α-methylalanine | Mala |
| L-α-methylcysteine | Mcys | L-α-methylasparagine | Masn |
| L-α-methylglutamine | Mgln | L-α-methyl-t-butylglycine | Mtbug |
| L-α-methylhistidine | Mhis | L-methylethylglycine | Metg |
| L-α-methylisoleucine | Mile | L-α-methylglutamate | Mglu |
| D-N-methylglutamine | Dnmgln | L-α-methylhomophenylalanine | Mhphe |
| D-N-methylglutamate | Dnmglu | N-(2-methylthioethyl)glycine | Nmet |
| D-N-methylhistidine | Dnmhis | N-(3-guanidinopropyl)glycine | Narg |
| D-N-methylisoleucine | Dnmile | N-(1-hydroxyethyl)glycine | Nthr |
| D-N-methylleucine | Dnmleu | N-(hydroxyethyl)glycine | Nser |
| D-N-methyllysine | Dnmlys | N-(imidazolylethyl)glycine | Nhis |
| N-methylcyclohexylalanine | Nmchexa | N-(3-indolylyethyl)glycine | Nhtrp |
| D-N-methylornithine | Dnmorn | N-methyl-γ-aminobutyrate | Nmgabu |
| N-methylglycine | Nala | D-N-methylmethionine | Dnmmet |
| N-methylaminoisobutyrate | Nmaib | N-methylcyclopentylalanine | Nmcpen |
| N-(1-methylpropyl)glycine | Nile | D-N-methylphenylalanine | Dnmphe |
| N-(2-methylpropyl)glycine | Nleu | D-N-methylproline | Dnmpro |
| D-N-methyltryptophan | Dnmtrp | D-N-methylserine | Dnmser |
| D-N-methyltyrosine | Dnmtyr | D-N-methylthreonine | Dnmthr |
| D-N-methylvaline | Dnmval | N-(1-methylethyl)glycine | Nval |
| γ-aminobutyric acid | Gabu | N-methyla-napthylalanine | Nmanap |
| L-t-butylglycine | Tbug | N-methylpenicillamine | Nmpen |
| L-ethylglycine | Etg | N-(p-hydroxyphenyl)glycine | Nhtyr |
| L-homophenylalanine | Hphe | N-(thiomethyl)glycine | Ncys |
| L-α-methylarginine | Marg | penicillamine | Pen |
| L-α-methylaspartate | Masp | L-α-methylalanine | Mala |
| L-α-methylcysteine | Mcys | L-α-methylasparagine | Masn |
| L-α-methylglutamine | Mgln | L-α-methyl-t-butylglycine | Mtbug |
| L-α-methylhistidine | Mhis | L-methylethylglycine | Metg |
| L-α-methylisoleucine | Mile | L-α-methylglutamate | Mglu |
| L-α-methylleucine | Mleu | L-α-methylhomophenylalanine | Mhphe |
| L-α-methylmethionine | Mmet | N-(2-methylthioethyl)glycine | Nmet |
| L-α-methylnorvaline | Mnva | L-α-methyllysine | Mlys |
| L-α-methylphenylalanine | Mphe | L-α-methylnorleucine | Mnle |
| L-α-methylserine | mser | L-α-methylornithine | Morn |
| L-α-methylvaline | Mtrp | L-α-methylproline | Mpro |
| L-α-methylleucine | Mval Nnbhm | L-α-methylthreonine | Mthr |
| N-(N-(2,2-diphenylethyl)carbamylmethyl-glycine | Nnbhm | L-α-methyltyrosine | Mtyr |
| 1-carboxy-1-(2,2-diphenyl ethylamino)cyclopropane | Nmbc | L-N-methylhomophenylalanine | Nmhphe |
| N-(N-(3,3-diphenylpropyl)carbamylmethyl(1)glycine | Nnbhe | D/L-citrulline | D/Lctr |

As is well accepted in the art in the molecular context, the term "residue", as used herein, refers to a portion, and typically a major portion of a molecular entity, such as molecule or a part of a molecule such as a group, which has underwent a chemical reaction and is now covalently linked to another molecular entity. In the context of the present invention, a residue is an equivalent term to a monomer comprising the polymer. For example, the molecular entity can be an amino acid molecule, and the portion of the amino acid which forms a part of a polypeptide chain (a polymer) after the formation of the polypeptide chain, is an amino acid residue (a monomer). An amino acid residue is therefore that part of an amino acid which is present in a peptide sequence upon reaction of, for example, an alpha-amine group thereof with a carboxylic group of an adjacent amino acid in the peptide sequence, to form a peptide amide bond and/or of an alpha-carboxylic acid group thereof with an alpha-amine group of an adjacent amino acid in the peptide sequence, to form a peptide amide bond. Similarly, the term "residue" refers to the major part of a hydrophobic moiety, such as, for example the acyl part of a fatty acid.

As used herein, the phrase "moiety" describes a part, and in exemplary embodiments a major part of a chemical entity or compound, which typically has certain functionality or distinguishing features.

As used herein, the phrase "hydrophobic moiety" describes a chemical moiety that has a minor or no affinity to water, that is, which has a low or no dissolvability in water and often in other polar solvents. Exemplary suitable hydrophobic moieties for use in the context of the present embodiments, include, without limitation, hydrophobic moieties that consist predominantly of one or more hydrocarbon chains and/or aromatic rings, and one or more functional groups which may be non-hydrophobic, but do not alter the overall hydrophobicity of the hydrophobic moiety. Representative examples include, without limitation, fatty acids, hydrophobic amino acids (amino acids with hydrophobic side-chains), alkanes, alkenes, aryls and the likes, as these terms are defined herein, and any combination thereof.

The term "side-chain", as used herein with reference to amino acids, refers to a chemical group which is attached to the α-carbon atom of an amino acid. The side-chain is unique for each type of amino acid and typically does not take part in forming the peptide bond in a naturally occurring protein or polypeptide, but can be used to form a link between monomers in the polymer presented herein in cases the side-chain comprises a suitable functional group. For example, the side chain for glycine is hydrogen, for alanine it is methyl, for valine it is isopropyl, for phenylalanine it is benzyl, and the side chain for lysine can be regarded as an amino-butyl group, e.g., having an available amine group. For the specific side chains of all amino acids reference is made to A. L. Lehninger's text on Biochemistry (see, chapter 4).

The term "linear" as used herein in the context of the polymers, refers to a non-cyclic polymer, i.e., a polymer which have two termini and its backbone or amino-acid side-chains do not form a closed ring.

According to certain embodiments of the present invention, the linear or cyclic polymer comprises a plurality of amino acid residues and one or more hydrophobic moiety residues as described hereinabove, wherein at least one of the hydrophobic moiety residues is being covalently linked to one of the amino acid residues via an amine group in the side-chain thereof. According to some embodiments, the amine group in the side-chain of the amino acid residue is the epsilon amine group of a lysine residue.

The term "cyclic" as used herein in the context of the polymer, refers to a polymer that comprises an intramolecular covalent bond between two non-adjacent residues (monomers) therein, forming a cyclic polymer ring.

In the context of the present embodiments the polymer comprises residues of amino acids and hydrophobic moieties which constitute the monomers of the polymer. The term residue is meant to encompass other chemical moieties which form a part of the polymer, and which do not fall under the definition of amino acid or hydrophobic moiety, as these are defined herein. For example, the cyclic polymer may be "closed" or cyclized by means of a multifunctional or bifunctional moiety that will form a part of the cyclic polymer once it is cyclized.

According to some embodiments with respect to the cyclic polymer, the polymer includes at least one residue that has a functional group, which is referred to herein as the first functional group, and at least one residue that has a second functional group, whereas the first and second functional groups are covalently linked therebetween, thereby forming a cyclic polymer.

As used herein, the phrase "functional group" describes a chemical group that is capable of undergoing a chemical reaction that typically leads to a bond formation. The bond, according to exemplary embodiments, is a covalent bond. Chemical reactions that lead to a bond formation include, for example, nucleophilic and electrophilic substitutions, nucleophilic and electrophilic addition reactions, addition-elimination reactions, cycloaddition reactions, rearrangement reactions and any other known organic reactions that involve a functional group.

The first and second functional groups may form a part of an amino acid residue and/or a hydrophobic moiety residue in the polymer, or any other element in the polymer which does not fall under the definition of amino acid or hydrophobic moiety, such as, for example, a linking moiety. The first and second functional groups are selected such that they are capable of forming a covalent bond therebetween or therefrom. For example, either the first or the second functional group can be a binding pair of an amine and a carboxyl which form an amide (peptide bond), a hydroxyl and a carboxyl which form an ester, or a an amine and an aldehyde which form an imine (Schiff base).

According to some embodiments, the first functional group is an amine group and the second functional group is a carboxyl group. Alternatively, the first functional group is a carboxyl group and the second functional group is an amine group. Therefore the first functional group and the second functional group can form a peptide bond therebetween.

The amine group, in the context of the first and/or second functional group, can originate from an N-alpha amine of an amino acid residue, or from an amine on the side-chain of an amino acid residue, such as found for example, in lysine and ornithine. Alternatively, the amine can stem from a hydrophobic moiety residue, such as, for example, an amino-fatty acid. Similarly, the carboxyl group, in the context of the first and/or second functional group, can originate from a C-alpha carboxyl of an amino acid residue, or from a carboxyl on the side-chain of an amino acid residue, such as found for example, in aspartic acid and glutamic acid. Alternatively, the amine can stem from a hydrophobic moiety residue, such as, for example, an amino-fatty acid. Similarly, the carboxyl group can stem from a hydrophobic moiety residue, such as, for example, any fatty acid.

According to some embodiments of the present invention, one of the first or second functional groups is an amine on a hydrophobic moiety residue, and the other functional group is a carboxyl on an amino acid residue.

Unless stated otherwise, the use of the terms "polymer" and "polymers" herein refers to both the cyclic and/or the linear form thereof.

The polymer, according to the present embodiments, may have two or more hydrophobic moiety residues, whereby at least one is linked to one amino acid at one end and to another amino acid residue at another end, and another may elongate the polymeric chain by being linked to either one of the termini thereof, for example to the N-alpha of a terminal amino acid residue and/or the C-alpha of a terminal amino acid residue. Optionally, a second hydrophobic moiety may be linked to a side-chain of an amino acid residue in the polymer.

The net positive charge of the polymer, which is one of the key characteristics of AMPs which were found to be linked to their activity, is maintained by having one or more positively charged amino acid residues in the polymer, optionally in addition to the positively charged N-terminus amine.

As used herein the phrase "positively charged amino acid" describes a hydrophilic amino acid with a side chain pKa value of greater than 7, namely a basic amino acid. Basic amino acids typically have positively charged side chains at physiological pH due to association with a hydronium ion. Naturally occurring (genetically encoded) basic amino acids include lysine (Lys, K), arginine (Arg, R) and histidine (His, H), while non-natural (non-genetically encoded, or non-standard) basic amino acids include, for example, ornithine, 2,3,-diaminopropionic acid, 2,4-diaminobutyric acid, 2,5,6-triaminohexanoic acid, 2-amino-4-guanidinobutanoic acid, and homoarginine.

In some embodiments of the present invention, all the amino acid residues in the polymer are positively charged amino acid residues. Exemplary polymers according to this embodiment include a plurality of lysine residues.

In some embodiment of the present invention, each of the residues in the polymer is linked to the other by a peptide bond.

The terms "peptide bond" and "amide bond" as used herein refer to an amide group, namely, a —(C=O)NH— group, which is typically formed by nucleophilic addition-elimination reaction between a carboxylic group and an amine group, as these terms are defined herein.

However, the polymers of the present embodiments may have other bonds linking the various components in the polymeric structure. Such non-peptidic bonds may render the polymer more stable while in a body or more capable of penetrating into cells. Thus, peptide bonds (—(C=O)NH—) within the polymer may be replaced, for example, by N-methylated amide bonds (—(C=O)NCH$_3$—), ester bonds (—C(R)H—C(=O)—O—C(R)—N—), ketomethylen bonds (—C(=O)CH$_2$—), aza bonds (—NH—N(R)—C(=O)—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—C(=O)—), peptide derivatives (—N(R)—CH$_2$—C(=O)—), wherein R is the "normal" side chain, naturally presented on the carbon atom. These modifications can occur at any of the bonds along the polymer chain and even several (2-3) at the same time.

In some of the present embodiments, all of the bonds in the polymer, linking the amino acid residues and hydrophobic moiety residues to each other, are peptide bonds. For example, in some embodiments, the polymer is made of an amino acid residue linked by a peptide bond to a hydrophobic moiety residue which in turn is linked to a second amino acid residue by another peptide bond. In another example, the polymer of the previous example is elongated by a second hydrophobic moiety residue which is linked to any one of the N- or C-termini by a peptide bond, etcetera.

The polymer, according to some embodiments, includes from 2 to 50 amino acid residues. According to other embodiments, the polymer includes from 2 to 8 amino acid residues and according to yet other embodiments from 2 to 6 amino acid residues.

The polymer, according to some embodiments, includes from 1 to 50 hydrophobic moiety residues. According to other embodiments, the polymer comprises from 1 to 12 hydrophobic moiety residues, and according to yet other embodiments from 1 to 8 hydrophobic moiety residues or from 1 to 6 hydrophobic moiety residues.

The hydrophobic moieties that are used in the context of some embodiments have one or more hydrocarbon chains, and are capable of linking to one or two other components in the polymer (e.g., one or two of an amino acid residue and another hydrophobic moiety) via two peptide bonds. These moieties therefore can have a carboxylic group at one end of the hydrocarbon chain (for linking a free amine group) and an amine group at the other (for linking a carboxylic acid group).

The hydrocarbon chain connecting the carboxylic and amine groups in such a hydrophobic moiety has from 4 to 30 carbon atoms in exemplary embodiments.

In some embodiments of the present invention, the hydrophobic moiety residue is a fatty acid residue wherein the hydrocarbon chain can be unbranched and saturated, branched and saturated, unbranched and unsaturated or branched and unsaturated. In some embodiments the hydrocarbon chain of the fatty acid residue is an unbranched and saturated chain having from 4 to 30 carbon atoms, and in exemplary embodiments from 4 to 20 carbon atoms. Non-limiting example of such fatty acid residues are butyric acid residue, such as γ-aminobutyric acid residue and α-aminobutyric acid residue, caprylic acid residue, lauric acid residue, palmitoleic acid residue and oleic acid residue.

In other embodiments, the fatty acid residue has an amine on the distal carbon of the hydrocarbon chain (with respect to the carboxylic acid group). Such a fatty acid residue is referred to herein as a ω-amino fatty acid residue. Again here the hydrocarbon chain of the ω-amino fatty acid residue may have from 4 to 30 carbon atoms.

The term "ω-amino-fatty acid" refers to linear amino fatty acids which have an amino group at the end-carbon thereof. Exemplary ω-amino-fatty acids include, without limitation, 4-amino-butyric acid, 6-amino-caproic acid, 8-amino-caprylic acid, 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid 4-amino-butyric acid, 6-amino-caproic acid, 8-amino-caprylic acid, 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid According to some embodiments of the present invention, the hydrophobic moiety is selected from the group consisting of 4-amino-butyric acid, 8-amino-caprylic acid and 12-amino-lauric acid and in exemplary embodiments is 8-amino-caprylic acid and 12-amino-lauric acid.

The linear polymers described herein can be represented collectively by the following general Formula I:

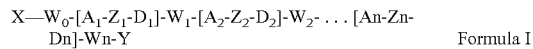

X—W$_0$-[A$_1$-Z$_1$-D$_1$]-W$_1$-[A$_2$-Z$_2$-D$_2$]-W$_2$- . . . [An-Zn-Dn]-Wn-Y      Formula I wherein:

n is an integer from 2 to 50, in exemplary embodiments from 2 to 12 and in other exemplary embodiments from 2 to 8;

A$_1$, A$_2$, . . . , An are each independently an amino acid residue, in exemplary embodiments a positively charged amino acid residue, and in other exemplary embodiments all of A$_1$, A$_2$, . . . , An are positively charged amino acid residues as discussed hereinabove, such as histidine residues, lysine residues, ornithine residues and arginine residues, and in some exemplary embodiments all the positively charged amino acid residues are lysine residues;

D$_1$, D$_2$, . . . , Dn are each independently a hydrophobic moiety residue, as defined and discussed hereinabove, or absent, provided that at least one such hydrophobic moiety residue exists in the polymer, and in exemplary embodiments at least one of the hydrophobic moiety residues is a ω-amino-fatty acid residue;

Connecting each monomer of the residue are linking moieties, denoted Z$_1$, Z$_2$, . . . , Zn and W$_0$, W$_1$, W$_2$, . . . , Wn, each of which independently linking an amino acid residue and a hydrophobic moiety residue or absent, in exemplary embodiments at least one of the linking moieties is a peptide bond and in some exemplary embodiments all the linking moieties are peptide bonds;

The fringes of the polymer, denoted X and Y, may each independently be hydrogen, an amine, an amino acid residue, a hydrophobic moiety residue, is another polymer having the general Formula I or absent.

Exemplary linear polymers according to the present embodiments are those having the structures presented hereinbelow:

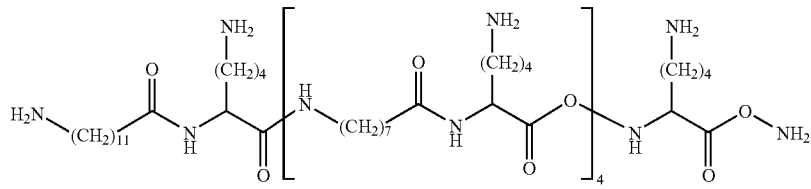

which can also be referred to as $NC_{12}K(C_8K)_4KNH_2$; and

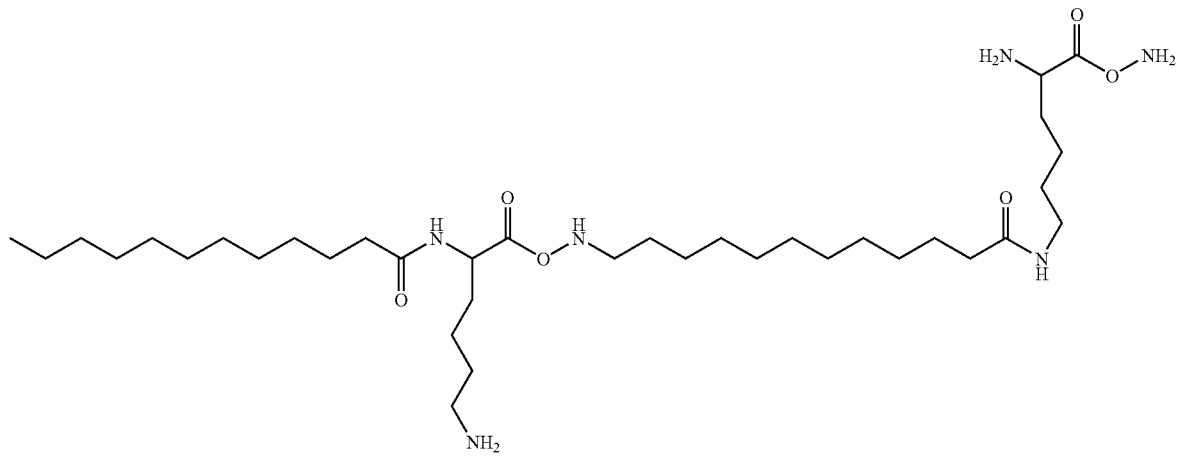 [SMILES: CCCCCCCCCCCC(=O)NC(CCCCN)C(=O)ONCCCCCCCCCCCC(=O)NCCCCC(N)C(=O)ON]

which can also be referred to as $C_{12}KNC_{12}K(\epsilon)NH_2$.

Other exemplary linear polymers are presented in U.S. Patent Application Nos. 2006/0074021 and 2007/0032428, WO 2006/035431 and U.S. Provisional Patent Application Nos. 60/924,087 and 60/924,088.

The cyclic polymers described herein can be represented collectively by the following general Formula II:

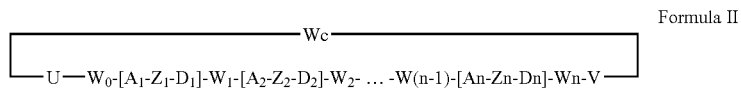

Formula II wherein:

n is an integer from 2 to 50, in exemplary embodiments from 2 to 12 and in other exemplary embodiments from 2 to 8;

$A_1, A_2, \ldots, An$ are each independently an amino acid residue, in exemplary embodiments a positively charged amino acid residue, and in other exemplary embodiments all of $A_1, A_2, \ldots, An$ are positively charged amino acid residues as discussed hereinabove, such as histidine residues, lysine residues, ornithine residues and arginine residues, and in some exemplary embodiments all the positively charged amino acid residues are lysine residues;

$D_1, D_2, \ldots, Dn$ are each independently a hydrophobic moiety residue, as defined and discussed hereinabove, or absent, provided that at least one such hydrophobic moiety residue exists in the polymer, and in exemplary embodiments at least one of the hydrophobic moiety residues is a ω-amino-fatty acid residue;

Connecting each monomer of the residue are linking moieties, denoted $Z_1, Z_2, \ldots, Zn$ and $W_1, W_2, \ldots, Wn-1$, each of which independently linking an amino acid residue and a hydrophobic moiety residue or absent.

U is selected from the group consisting of the first functional group, as defined hereinabove, an amino acid residue having that first functional group, a hydrophobic moiety residue having that first functional group, and a linking moiety having that first functional group, or absent.

Similarly, V is selected from the group consisting of the second functional group, an amino acid residue having that second functional group, a hydrophobic moiety residue having that second functional group, and a linking moiety having that second functional group, or absent.

The linking moiety $W_0$ is linking any one of $A_1$, $Z_1$ and $D_1$ to U, or absent, the linking moiety Wn is linking any one of An, Zn and Dn to V, or absent; and Wc is a cyclizing moiety which is a type of a linking moiety.

The moieties which close the polymer into a cyclic polymer, denoted U and V, may each independently be absent or be an amino acid residue or a hydrophobic moiety residue, provided they each has a functional group, referred to hereinabove as the first and second functional groups, which can form a covalent bond therebetween. Thus, such amino acid residues and/or hydrophobic moiety residues can form together a unique linking moiety denoted herein as Wc, which is referred to herein as the cyclizing moiety.

As used herein, the phrase "linking moiety" describes a chemical moiety, group or a bond, as defined herein, which links between two residues or monomers. The linking moiety can thus be, for example, formed upon reacting two functional groups; each forms a part of another monomer or residue, thus linking the two monomers or residues. For example, an amine group on one monomer can form a peptide bond with a carboxyl group on another monomer and the resulting moiety is a peptide bond linking moiety.

According to some embodiments of the present invention, at least one of the linking moieties in the polymers presented herein is a peptide bond, and more typically all the linking moieties are peptide bonds.

The phrase "cyclizing moiety", denoted Wc in Formula II, refers to a chemical moiety which is formed when two residues in Formula II are linked therebetween, thereby forming the cyclic polymer. The cyclizing moiety may be, for example, a bond which is formed between two functional groups, such as, for a non-limiting example, an amide (peptide bond), a carboxylate (ester), a carbamate, an ether and the likes.

The two functional groups which form Wc, can stem from U and V, $W_0$ and Wn, or $A_1$, $Z_1$ and $D_1$ and An, Zn or Dn, or any combination thereof. Alternatively, the cyclizing moiety may comprise a residue of a multifunctional (as at least bifunctional) moiety which forms bonds with functional groups on U and V, $W_0$ and Wn, or $A_1$, $Z_1$ and $D_1$ and An, Zn or Dn, such as, for a non-limiting example, p-aminobenzoic acid or ethyleneglycol.

According to some embodiments of the present invention the cyclizing moiety, denoted Wc, is a peptide bond which is formed from an amine group on either U of V, and a carboxyl on either V or U.

Hence, for better clarity, the phrase "cyclic polymer" as used herein in the context of the polymer, refers to a polymer that comprises an intramolecular covalent bond which forms a part of a cyclizing moiety. The cyclizing moiety is positioned between two non-adjacent residues therein, forming a cyclic polymer ring that comprises at least two amino acid residues, at least one hydrophobic moiety residue, a cyclizing moiety and optionally further comprise a plurality of linking moieties and other residues. The cyclizing moiety may connect backbone to any two residues in the polymer via backbone atoms, side-chain atoms or a combination thereof.

According to some embodiments of the present invention cyclic polymers are polymers in which n is an integer from 2 to 5, the amino acid residues are all lysine residues, and the hydrophobic moiety residues are all 12-amino-lauric acid residues.

Exemplary cyclic polymers according to some embodiments of the present invention are those having the structures presented hereinbelow:

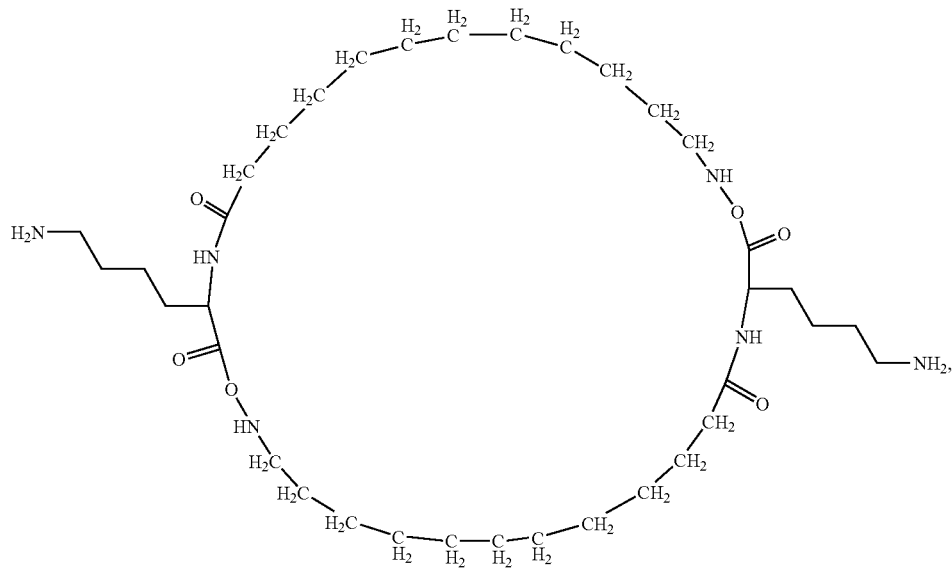

which can also be referred to as Cyclic-$(NC_{12}K)_2$; and

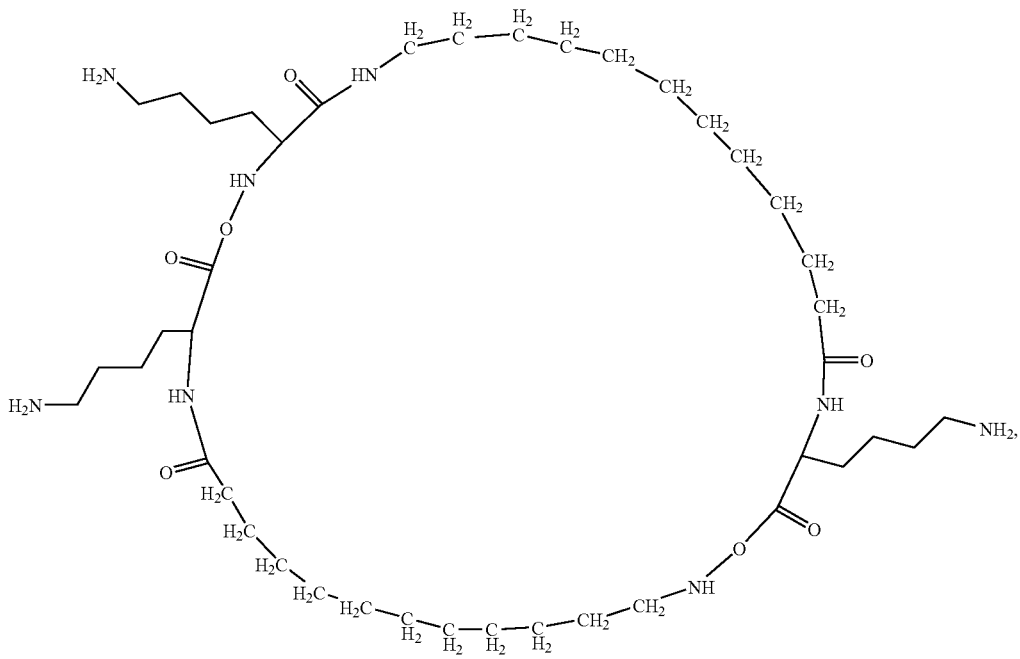

which can also be referred to as Cyclic-$NC_{12}KKNC_{12}K$.

As discussed above, one or more of the hydrophobic moiety residues may be attached to a side chain of one or more of the amino acid residues of the polymer, i.e., act as a branch of the main linear or cyclic polymer.

The polymers according to embodiments of the present embodiments can be readily synthesized as demonstrated for structurally similar antimicrobial polymers in U.S. Patent Application Nos. 2006/0074021 and 2007/0032428, WO 2006/035431 and U.S. Provisional Patent Application Nos. 60/924,087 and 60/924,088, and in the Examples section that follows hereinbelow. For example, polymers in which the linking moieties are peptide bonds, and hence resemble natural and synthetic peptides in this respect, can be prepared by classical methods known in the art for peptide syntheses. Such methods include, for example, standard solid phase techniques. The standard methods include exclusive solid phase synthesis, partial solid phase synthesis methods, fragment condensation, classical solution synthesis, and even by recombinant DNA technology. See, e.g., Merrifield, *J. Am. Chem. Soc.*, 85:2149 (1963), incorporated herein by reference. Solid phase peptide synthesis procedures are well known in the art and further described by John Morrow Stewart and Janis Dillaha Young, Solid Phase Peptide Syntheses (2nd Ed., Pierce Chemical Company, 1984).

Solid phase peptide syntheses techniques are particularly suitable for preparing the polymers according to some embodiments of the present invention as these polymers are already attached to a water-insoluble matrix. Characteristic to the more widely used solid-phase synthesis techniques, the polymers presented herein are attached to the solid support resin beads (water-insoluble matrix) via the C-terminus, which is attached to the resin beads via an amide linking group.

An example of such matrix-bound polymer according to some embodiments of the present invention is having the formula:

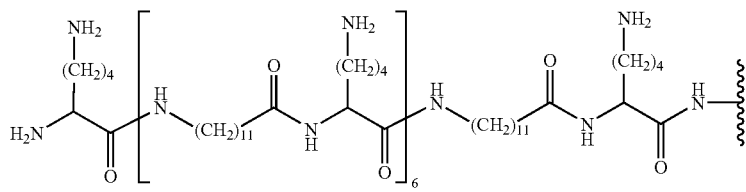

wherein the adulating line represents the linkage to the resin bead, and which can also be referred to as $K(NC_{12}K)_7NH$—.

Water-Insoluble Matrix

The polymer(s) selected for attachment to the water-insoluble matrix. Such a water-insoluble matrix serves as a solid support for the polymer, namely, it provides a stationary object with respect to the aqueous solution and the various chemicals dissolved in it. The water-insoluble matrix allows performing a continuous and/or repetitive contact of the aqueous solution containing the microorganisms with the polymer(s) attached thereto, as well as maintaining the polymer(s) affixed, thus eliminating loss of the polymer(s) due to leaching.

According to some embodiments, the water-insoluble matrix comprises a granular and/or porous substance or mixture of substances, which allows a relatively free flowing of the aqueous solution therethrough. Indeed, in many applications where concentration of microorganisms is an essential step, the aqueous solution to be tested is required to pass through the matrix in order to allow the microorganisms in the solution to come in contact with the matrix and the elements which are attached thereto, and in many cases large quantities of the solution must be passed through in order to obtain a concentration which is necessary for detection.

Many commercially available solid-phase synthesis columns, purification and ion-exchange columns, are packed with granular and/or porous water-insoluble and water-permeable matrices which are suitable for polymer immobilization applications, or can readily be modified so as to be suitable for polymer immobilization, and therefore are suitable for use as the water-insoluble matrix in the context of the present invention.

Such granular and/or porous water-insoluble matrices are well known in the art and are used in various applications such as filtration and chromatography. Representative examples include, without limitation, organic substances such as nylons, polystyrenes, polyurethanes and other synthetic polymers and co-polymers, activated carbon, cellulose, agarose, chitin, chitosan and collagen, and inorganic substances such as glass, plastic, metal, zeolite, silica, alumina, titania, zirconia, calcium alginate and celite.

Most nylons are condensation copolymers formed by reacting equal parts of a diamine and a dicarboxylic acid, such that amide bonds are formed at both ends of each monomer in a process analogous to polypeptide biopolymers. The most common variant is nylon 6,6, also called nylon 66, in which the diamine (hexamethylene diamine) and the diacid (adipic acid) each donate 6 carbons to the polymer chain. As with other regular copolymers like polyesters and polyurethanes, the repeating unit consists of one of each monomer. Substituted diamines and dicarboxylic acids are used so as to produce nylons with a variety of free functional groups along the polymeric chain.

Polystyrene is a polymer made from the monomer styrene, a liquid hydrocarbon that is commercially manufactured from petroleum. At room temperature, polystyrene is normally a solid thermoplastic, but can be melted at higher temperature for molding or extrusion, and then re-solidified. Substituted styrene can be used to form an aromatic polymer with a variety of free functional groups along the polymeric chain.

Activated carbon (also called activated charcoal) is a general term which includes carbonaceous material mostly derived from charcoal. It denotes a material which has an exceptionally high surface area, typically determined by nitrogen adsorption, and is highly microporous. Sufficient activation for useful applications may come solely from the high surface area, though often further chemical treatment is used to enhance the adsorbing properties of the material. Chemically, activated carbon binds materials by Van der Waals force, specifically London dispersion force, and saturated active carbon can be regenerated by heating.

Cellulose is a chief constituent of the cell walls of plants (raw cotton is composed of 91% pure cellulose). Chemically, it is a long-chain polysaccharide (polymer) carbohydrate of beta-glucose. Insoluble in water and other ordinary solvents, it exhibits marked properties of absorption. Because cellulose contains a large number of hydroxyl groups, it reacts with acids to form esters and with alcohols to form ethers. Cellulose derivatives include guncotton, fully nitrated cellulose, used for explosives; celluloid (the first plastic), the product of cellulose nitrates treated with camphor; collodion, a thickening agent; and cellulose acetate, used for plastics, lacquers, and fibers such as rayon.

Chitin is one of the main components in the cell walls of fungi, the exoskeletons of insects and other arthropods, and in some other animals. It is a polysaccharide, made out of units of acetylglucosamine (more completely, N-acetyl-D-glucos-2-amine). These are linked together in $\beta$-1,4 fashion, the same as the glucose units that make up cellulose, so chitin may be regarded as a derivative of cellulose, with one hydroxyl group on each monomer replaced by an acetylamino group. This allows for increased hydrogen bonding between adjacent polymers, giving the material increased strength. The strength and flexibility of chitin is the reason it is the material of choice for surgical thread and a variety of water-insoluble matrices.

Chitosan is a linear polysaccharide composed of randomly distributed $\beta$-(1-4)-linked D-glucosamine (deacetylated unit) and N-acetyl-D-glucosamine (acetylated unit). Chitosan is produced commercially by deacetylation of chitin. The degree of deacetylation (% DA) in commercial chitosans is in the range 60-100%. The amino group in chitosan has a pKa value of about 6.5, and hence, chitosan is positively charged and soluble in acidic to neutral solution with a charge density dependent on pH and the % DA-value. Chitosan is therefore a bioadhesive which readily binds to negatively charged surfaces and compounds. Chitosan and its derivatives such as trimethylchitosan (where the amino group has been trimethylated), and quaternized chitosan have been used in delivery of therapeutic agents such as peptides and proteins, as well as for immobilizing purposes.

Zeolites is a family of hydrous aluminum silicate minerals that have high surface area and porous structure, and a highly organized three-dimensional structure of tetrahedral $SiO_4$ and $AlO_4$ linked to one another by a shared oxygen. More than 150 zeolite types have been synthesized and 48 naturally occurring zeolites are known. They are basically hydrated alumino-silicate minerals with an open structure that can accommodate a wide variety of positive ions, such as $Na^+$, $K^+$, $Ca^{2+}$, $Mg^{2+}$ and others. These positive ions are rather loosely held and can readily be exchanged for others in a contact solution. Some of the more common mineral zeolites include analcime, chabazite, heulandite, natrolite, phillipsite, and stilbite. An example mineral formula for natrolite is $Na_2Al_2Si_3O_{10}.2H_2O$. Zeolites can be modified by thermal and chemical treatments such as cation exchange or dealumination. The modified zeolites give the possibility of creating and regulating acid-base, hydrophobic-hydrophilic, and selective adsorption properties that are responsible for their structural diversity and extensive applications in catalytic reaction. Due to their high stability, porous structure and chemical diverseness of their surface, zeolites and surface modified derivatives thereof are used as molecular filters, chromatography, ion-exchange agents and for immobilizing enzymes and other proteins.

Other forms of organic polymers, copolymers and cross-linked derivatives thereof, and inorganic materials such as diatomaceous earths and other types of molecular sieves, typically used in various filtration applications, can be used in the form of microspheres, beads, granules and/or porous water-insoluble matrix, according to embodiments of the present invention, on or in which a polymer can be incorporated.

The term "incorporated", as used herein, refers to any mode of contact between the water-insoluble matrix and the polymer which achieves immobilization of the polymer with respect to the matrix, thus rendering a polymer insoluble, or in other words immobilized, and in some cases more protected and less cytotoxic, thus more stable in the context of the present embodiments. SPR-affinity measurements using liposomes as a model for mimicking bacterial membranes, showed high affinity binding of the resin-free polymers to the model membrane, with $K_{app}$ ranging from $10^4$ to $10^7$ $M^{-1}$ [5]. In an exemplary embodiment, binding of the polymer to the matrix is effected while substantially maintaining the polymer's affinity towards the microorganism.

Thus, incorporation of the polymer(s) in or on the matrix can be effected by attachment via several types of chemical bonding interactions, including covalent bonds, metal-mediated complexation, strong affinity-pair bonding and the likes, and in an exemplary embodiment by covalent bonding.

The polymer(s) can be incorporated in and/or on physical structural elements of a water-insoluble matrix. In cases where the structural elements of the matrix are granular but not porous, such as, for example, in cases where the matrix is made of solid spheres, beads or particles, the polymer(s) is incorporated on the surface of the beads or particles, and the aqueous solution that flows in the channels between the beads or particles comes in contact with the polymer(s), thus allowing the microorganisms in the polymer to bind to the polymer(s).

In cases where the structural element of the matrix is porous, such as, for example, in cases where the matrix is extruded zeolite blocks, carbonaceous blocks or solid plastic foam blocks, the polymer(s) can be incorporated in the cavities, on the inner surface of the innate inter-connected pores and channels which are characteristic to such matrices, as well as on the outer surface of the block, and the aqueous solution that flows in the inter-connected pores and channels comes in contact with the polymer(s).

In cases where the structural elements of the matrix are granular and porous, such as, for example, in cases where the matrix is zeolite granules or molecular sieves pellets, the polymer(s) is incorporated on the surface of the granules or pellets and in the inner surface of the pores and channels of these matrices, and the aqueous solution that flows between the granules or pellets as well as through them comes in contact with the polymer(s), thus allowing the microorganisms in the aqueous solution to bind to the polymer(s).

The matrix can have a form which is selected from the group consisting of a flat surface, a fiber, a tube, a bead, a sphere, a mesh, a net, a web, a grid, a lattice, a plexus, a screen and any combination thereof. Typically, the matrix will have a form which will increase the surface area and thus the probability of contacting a passing microorganism call with a matrix-bound polymer. Another consideration is a flow-rate, hence the matrix will typically have a form that allows the aqueous solution to flow through freely.

Covalent Attachment of the Polymer to the Matrix

According to embodiments of the present invention, the incorporation of the polymer to the water-insoluble matrix is effected by covalently attaching the polymer to the water-insoluble matrix (the solid support) by conventional methods known in the art for polymer immobilization. In practice, the process by which some polymers according to some embodiments of the present invention are produced is effected on a solid support resin, since the polymers are made by incremental elongation methods while attached to a solid support.

Exemplary immobilization techniques are described for example in U.S. Pat. Nos. 4,071,409, 4,090,919, 4,258,133, 4,888,285, 5,177,013, 5,310,469, 5,998,183, 6,905,733, and 6,987,079, U.S. Patent Application Publication No. 2003/0096383, and in Yan A-X. et al., 2002, *Applied Biochemistry and Biotechnology*, Vol. 101(2), pp. 113-130(18); and Ye, Yun-hua et al., 2004, *Peptide Science*, Vol. 41, pp 613-616, which are incorporated herein by reference as if fully set forth.

Briefly, polymer attachment by covalent bonding to the matrix, according to some embodiments of the present invention, is based on coupling two functional groups, as these are defined hereinbelow, one within the matrix (e.g., on its surface) and the other within the polymer (e.g., along its main-chain or side-chains), either directly or via a spacer or a linker. The spacer can be, for example, a bifunctional moiety, namely, a compound having at least two functional groups which are capable of forming covalent bonds with functional groups of both the matrix and the polymer.

The polymer can be attached to the water-insoluble matrix by any one of the available functional groups along the structure of the polymer, and for example, by one of the termini either directly or, for example, via one of the capping moieties denoted X and Y in general Formula I.

Non-limiting examples for functional groups which can be designed into the polymer structure and can be utilized for direct or indirect coupling with a solid support matrix include both functional groups derived from side chains of certain amino-acid residues, functional groups derived from the hydrophobic moieties and functional groups derived from the N-terminus or the C-terminus of the polymer. These include, for example, amine (stemming from side-chain of the positively charged amino-acids lysine and arginine, the ω-amine of ω-amino-fatty acids and the N-terminus) and amides (stemming from the peptide linking moieties).

Other functional groups can be chemically introduced to the polymer so as to suit the type and chemistry of the matrix. Representative examples of such functional groups include, without limitation, amine, acyl, aldehyde, alkoxy, thioalkoxy, alkyl, alkenyl, C-amide, N-amide, carboxyl, diol, farnesyl, geranylgeranyl, guanidine, hydroxyl, thiohydroxy (thiol), imidazole, indole, phosphate and sulfate, as these are defined herein.

Non-limiting examples for functional groups which exist on the surface of the water-insoluble matrix material, or can be introduced thereto, and can be utilized for direct or indirect conjugation with an polymer include, without limitation, hydroxyl (present on the surface of organic and inorganic matrices containing silica, alumina and other metal oxides), amine (which can be chemically introduced to many inorganic matrices), acyl, aldehyde, alkoxy, thioalkoxy, alkyl, alkenyl, C-amide, N-amide, carboxyl, diol, farnesyl, geranylgeranyl, guanidine, hydroxy, thiohydroxy, imidazole, indole, phosphate and sulfate.

As used herein, the term "amide" refers to a R'—C(═O)—NR"R'" group, where R', R" and R'" are each hydrogen, amine, amide, alkyl, alkenyl, cycloalkyl, aryl, heteroaryl (bonded through a ring carbon) or heteroalicyclic (bonded through a ring carbon) as defined hereinbelow, or R' and one of R" and R'" may be connected so as to form a heteroaryl or heteroalicyclic ring.

As used herein, the term "amine" refers to an NR'R" group where R' and R" are as defined herein.

The term "alkyl" as used herein, describes a saturated aliphatic hydrocarbon including straight chain and branched chain groups. In exemplary embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In other exemplary embodiments, the alkyl is a medium size alkyl having 1 to 10 carbon atoms and in some exemplary embodiments, unless otherwise indicated, the alkyl is a lower alkyl having 1 to 5 carbon atoms.

The term "alkenyl" refers to an alkyl group which consists of at least two carbon atoms and at least one carbon-carbon double bond.

The term "cycloalkyl" describes an all-carbon monocyclic or fused ring (i.e., rings which share an adjacent pair of carbon atoms) group where one or more of the rings does not have a completely conjugated pi-electron system.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system.

The term "aryl" describes an all-carbon monocyclic or fused-ring polycyclic (i.e., rings which share adjacent pairs of carbon atoms) groups having a completely conjugated pi-electron system.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include triazine, pyrrole, furane, thiophene, imidazole, oxazole, thiazole, pyrazole, pyridine, pyrimidine, quinoline, isoquinoline and purine.

As used herein, the term "hydroxyl" refers to an —OH group.

As used herein, the term "thiohydroxyl" or "thiol" refers to an —SH group.

As used herein, the term "carboxyl" refers to a —C(=O)OR' group, where R' is as defined herein.

As used herein, the term "aldehyde" refers to a —C(=O)—H group.

As used herein, the term "diol" refers to a vicinal diol which is a —CR'(OH)—CR"(OH)— group.

As used herein, the term "carbonyl" refer to a —C(=O)-alkyl group, as defined hereinabove.

The term "alkoxy" as used herein describes both an —O-alkyl and an —O-cycloalkyl, as defined hereinabove.

As used herein, the term "thioalkoxy" describes both a —S-alkyl, and a —S-cycloalkyl, as defined hereinabove.

The term "farnesyl", as used herein, refers to the fatty residue of fernesene, which can be used in the polymer as a hydrophobic moiety.

The term "geranylgeranyl", as used herein, refers to the fatty residue of geranylgeranene, which can be used in the polymer as a hydrophobic moiety.

The term "guanidine" refers to a —NR'C(=NR")—NR'"R* group, where R' and R" are as defined herein and R'" and R* are defined as either R' or R". In the context of the present invention, guanidine is a functional group on the side-chain of the positively charged amino-acid arginine, therefore it is preferably —NH—C(=NH)—NH$_2$.

As used herein, the term "imidazole" refers to the five-membered heteroaryl group that includes two non-adjacent nitrogen atoms. An imidazole residue can be found in the side-chain of the positively charged amino acid histidine.

As used herein, the term "indole" refers to refers to a bi-cyclic heteroaryl comprised of fused phenyl and pyrrole groups. An indole residue can be found on the side-chain of the hydrophobic amino acid tryptophan.

The term "phosphate" describes a —O—P(=O)(OR')(OR") group, with R' and R" as defined herein.

As used herein, the term "sulfate" refers to a —O—S(=O)$_2$—O—R', with R' as defined herein.

Aqueous Solution

Once the polymer is attached to the matrix the aqueous solution which comprises the microorganism is contacted therewith. The aqueous solution containing the microorganism(s) is the media which is to come in contact with the matrix, and according to some embodiments is required to flow through the matrix.

The aqueous solution can be any solution which may come in contact with a microorganism and possibly retain viability of same.

According to some embodiments of the present invention, the aqueous solution is water from various sources and for various uses, wherein the sanitary condition thereof is of interest. Such water include, for a non-limiting example, potable water, irrigation water, reservoir water, natural source water (e.g., a spring, a well, a running stream and a lake), swimming pool water, hot-tub water, fountain water and the likes, as well as industrial and/or household sewage, wastewater, spent water and the likes.

According to other embodiments of the present invention, the aqueous solution is a liquid food product, such as a natural or artificial beverage, juice, milk and the likes.

According to yet other embodiments of the present invention, the aqueous solution is a bodily fluid which requires a detection and identification of a potential contamination/infection by a (pathogenic) microorganism.

Such bodily fluids include, without limitation, a blood sample, a urine sample, a spinal fluid sample, a saliva sample, tears sample, an amniotic fluid sample and other biological samples which can, if not in a liquid form, be solubilized, suspended, pulverized or otherwise liquefied.

Biological samples which comprise for example a cellular sample of tissue or fluid isolated from a can also be applied. A non-limiting example, bone marrow, plasma, serum, spinal fluid, lymph fluid, the external sections of the skin, respiratory, intestinal, and genitourinary tracts, tears, saliva, milk, blood cells, synovial cell fluid, tumors, organs such as synovial tissue and also samples of in vivo cell culture constituents, cell-lines, culture medium and cultured cells or cultured microbical cells (e.g., such as included in biochemical or microbial assays).

Biologic Viability

As discussed hereinabove, the design and selection of polymer(s) for the embodiments presented herein, can afford a matrix-polymer construct that can bind to the microorganism's membrane while not effecting cell death. Hence, according to some embodiments of the present invention, the microorganisms are concentrated by means of binding to the polymer-loaded matrix while maintaining their biologic viability, or in other words, the microorganisms which are captured by the polymer-loaded matrix can still proliferate if given the appropriate conditions for growth.

Release and Regeneration

In order to exploit this attribute of maintaining the biologic viability of the captured microorganisms, these are released from the polymer-loaded matrix by means of elution, wash or simply incubating the bacterial on the matrix. The cell release process can be effected by passing a solution containing a releasing substance, such as ethanol, LPS (lipopolysaccharides) or a mixture of salts and organic solvents. Typically, the cell release process is performed by passing a solution of 70% ethanol through the matrix, as demonstrated in the Examples section that follows below.

The ability to release the captured microorganisms from the polymer-loaded matrix allows for the regeneration and reuse of the polymer-loaded matrix for another capturing cycle(s) with similar or different sample solutions.

As demonstrated in the Examples section that follows, at least 10 repetitive binding and releasing cycles achieved reproducible microbial-capturing results using a resin-bound polymer according to embodiments of the present invention.

Microorganism Capturing Device

The method of concentrating microorganisms in a liquid sample, according to some embodiments of the present invention, can be implemented via designated devices which are designed for the purpose of concentrating microorganisms using the matrix-bound polymers as presented herein.

These devices are free of the drawbacks plaguing presently used to concentrate microorganisms by virtue of having the capacity to allow large volumes of aqueous solutions to pass therethrough while sifting-out the microorganisms in the solution regardless of their scarcity and without requiring long incubation periods.

Hence, according to another aspect of the present invention, there is provided a device for concentrating microorganisms which includes a casing or a number of casings and the water-insoluble matrix, having the polymer attached thereto as presented hereinabove, embedded in the casing(s), wherein the matrix is selected and configured so as to allow an aqueous solution which comprises microorganisms to flow through the matrix in the casing(s), and thereby allowing the microorganisms to bind to polymer on the matrix.

Such devices can take many shapes and form, best suited for their use. According to some embodiments of the present invention, the device is a filter-tube having two compartments separated by a perforated support (filter) which keeps particles of a water-insoluble matrix material from passing therethrough but allowing an aqueous solution to flow through freely by gravitation or centrifugal force. A microorganism-bearing solution is placed in the upper compartment over the filter, and thereby come in contact with the polymer-loaded matrix particles, and after an incubation period the solution is forced through the filter and into the lower compartment, leaving the microorganism bound to the polymer on the matrix. An example of such device is illustrated in FIG. 1.

FIG. 1 is a simplified illustration of an exemplary device for concentrating microorganisms, or microorganism capturing device, according to some embodiments of the present invention. Microorganism-capturing device 10, designed to capture microorganism in a liquid aqueous solution sample, is composed of a resin-bound polymer 12 which is packed in a centrifuge filter tube 14 having a filter 16. Polymer-loaded resin beads 18 are packed over filter 16, and a liquid sample containing microorganism 20 is contacted and incubated with beads 18 to allow microorganism 20 to be captured by polymer 12. The liquid sample is concentrated by means of centrifugation and filtrate 22 is removed. Microorganism 20 is released from polymer 12 and microorganism 20 is collected in filtrate 24.

Other devices according to some embodiments of the present invention, can take the shape of a flow-through tubular object for a casing, having an inlet on one side and an outlet on the other side for allowing a microorganism-bearing solution to enter and exit the casing. The casing is delimitated by two perforated barriers (filters) which together with the casing constitute a compartment in which polymer-loaded particles of a water-insoluble matrix are packed. Upon flowing (passing) the solution via the inlet and through the device, microorganisms are captured on the matrix, and a solution depleted therefrom exits the device via the outlet, thereby concentrating the microorganisms in the device.

Method of Detection and Identification

Devices such as presented herein designed to concentrate microorganisms, can be utilized in routine procedure for detection and identification of microorganisms in liquid samples (aqueous solutions) as presented hereinabove.

Hence, according to yet another aspect of the present invention, there is provided a method for detection and identification of microorganisms in an aqueous solution which is effected by:

(a) passing the aqueous solution containing the microorganisms through a device as presented herein, thereby binding the microorganisms to the polymer on the matrix embedded therein; and (b) identifying the bound microorganism.

The purpose of the device is to concentrate the microorganism in a rapid and efficient manner so as to provide a measurable level of cells suitable and sufficient in terms of detectable levels for any given technique for identification of microorganism to be applied to the concentrated sample.

Some microorganism-identification techniques require the microorganism to be manipulated, plated and/or multiply, hence the method presented herein may include an additional microorganism-release step, performed as presented hereinabove. Such a step can also be used simply to regenerate the device for subsequent use(s).

Exemplary techniques, well known in the art for detecting and identifying microorganisms include, without limitation, visual inspection and identification, DNA amplification (PCR and real-time-PCR) techniques, morphological identification techniques, biochemical identification techniques, microbiological identification techniques and immunological identification techniques.

Since the volume of the sample entering the microorganism-concentrating device can be measured, and the amount of microorganism cells captured by the device can be assessed by methods known in the art, as demonstrated in the Examples section that follows, the result of the detection and identification of the microorganism can result in a quantitative All the methods and devices presented herein, are characterized by several attributes which offer significant advantages over presently know methods and devices for concentrating or depleting microorganisms from an aqueous solution. One of these attributes is that microbial capturing is not based on size discrimination, namely size cut-off of a concentrating membrane but rather of chemical affinity. This attribute relieves the requirement of low particulate levels from the aqueous sample, or allows larger quantities of aqueous solution to be concentrated without the limitation of membrane blockage due to particulate therein.

This improvement also affects the time period which is required for microbial concentration and depletion, and the flow-rate at which solutions can be passed through the polymer-loaded matrix, after contacting (incubation) in cases where the concentration/depletion is conducted under stationary incubation conditions, or during the concentration/depletion process in cases where the concentration/depletion is conducted under continuous flow conditions.

The term "flow" and the phrase "flow rate", as used herein in the context of fluid flow, refer to the capacity of a device or a system to pass a volume unit of a liquid therethrough at a give time unit, typically measured in units of ml or liter per minute or hour. The flow rate at which an aqueous solution can pass through a polymer-loaded matrix according to some embodiments of the present invention, depends on the physical characteristics of the solution (suspended particulates, viscosity and thickness, temperature and the likes), on the physical characteristics of the device (diameter, length of travel distance and the likes) and on the characteristics of the matrix, namely the amount, size, shape, composition and compactness of the matrix, particularly when using small matrix particles such as, for example, beads, fibers and meshes.

Most currently used microbial-filtering (for concentrating and/or depleting) methods and devices are based on filters having a size cut-off based on the microorganisms' cells, these methods and devices employ 0.45 μm or 0.22 μm cut-off membranes. These membranes constitute one of the major weaknesses of these techniques, being highly sensitive to solution-borne particulates. Since the methods and devices presented herein employ microbial-capturing based on the interactions between the cell-membranes of the microorganisms and the polymers, rather than size discrimination, the volume of the sample which can come in contact with the polymer-loaded matrix is practically unlimited, and this is reflected also in the flow rate at which the concentration or depletion processes can be performed, which can be significantly higher without sacrificing the integrity of the device (by blockage due to particulates or the viscosity of the solution) or the accuracy and efficiency of the microbial-capturing process due to the effective and rapid interaction of the polymer with the microorganisms.

For example, a typical potable water sample will have a few single microbial cells per 100 ml, a typical sample size in most currently known microbial-detection methods and devices. In order to assure positive detection, one is required to process larger volumes of the sample, however the size-discriminating membrane used in those methods and devices will become clogged after a sample amount as small as 20 ml of typical potable water, which may not be sufficient for positive detection of dilute microbial presence. In sharp distinction, the present invention offers methods and devices that will not be limited by the above limitation, as demonstrated in the Examples section hereinbelow (see, RT-PCR measurements also presented in FIG. 10).

Hence, according to some embodiments of the present invention, the volume of the aqueous solution which is subjected to the concentrating and/or depletion methods, the detection and identification methods as well as the volume of the aqueous solution processed by the device, is not limited, and can exceed 10 liters.

Furthermore, according to some embodiments of the present invention, the density and size of particulates found in the aqueous solution is not a limiting factor in terms of the matrix' flow cross-section (pore-, channel-, opening-size in the matrix' material allowing liquid to flow therethrough), or the casing of the device (the physical barrier keeping the matrix material in place), and therefore can exceed the recommended limits determined for size-cutoff membrane filters (MF) based methods and devices.

It is expected that during the life of a patent maturing from this application many relevant methods and technique will be developed and the scope of the term concentration, detection and identification of microorganisms is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Resin-Bound Polymer Preparation:

The polymers were synthesized by a solid-phase method as previously described [6] using 4-methylbenzhydrylamine-resin beads with a diameter range of 50-100 μm (Novabiochem), applying the N-(9-fluorenyl)methoxycarbonyl (Fmoc) active ester chemistry on a 433A peptide synthesizer (Applied Biosystems) as previously described [7]. At the end of the synthesis, the resin was deprotected by incubation in dichloromethane:trifluoroacetic acid (50:50) mixture for 15 minutes at room temperature, washed twice with dichloromethane, twice with ethanol, placed under vacuum for 3 hours and stored at −20° C. Prior to use, the polymer-loaded resin beads were washed with saline.

A schematic and disproportional illustration of a resin bead loaded with a plurality of polymers, according to some embodiments of the present invention, is presented in Scheme 1 below.

Scheme 1

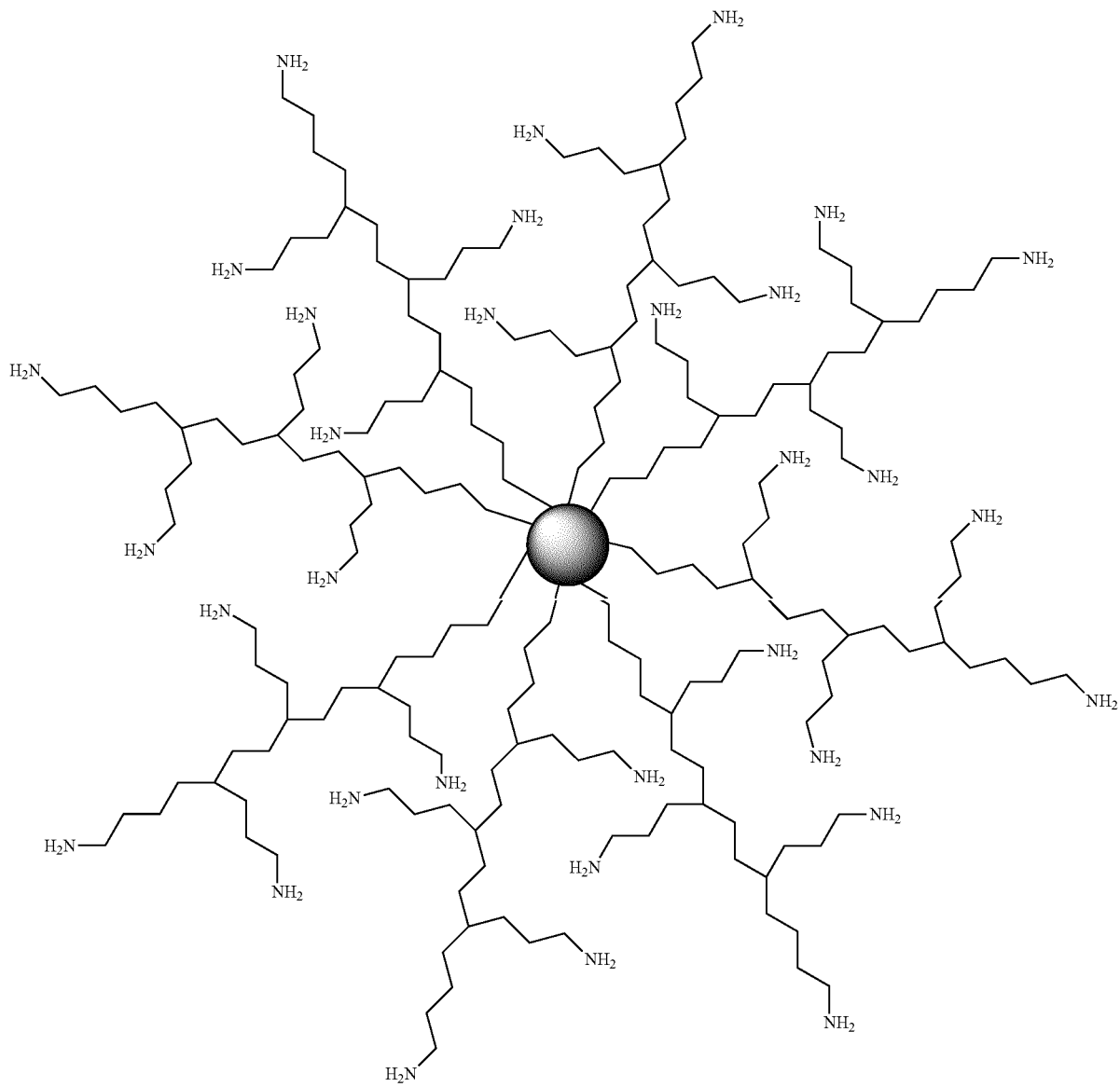

The polymers' sequence was verified post synthesis after cleavage from the resin, followed by LC-MS analysis (Alliance, Micromass ZQ—Waters) as previously described [7].

Briefly, HPLC chromatograms were performed on C18 columns (Vydak, 250 mm×4.6 or 10 mm) using a linear gradient of acetonitrile in water (1% per minute), both solvents contained 0.1% trifluoroacetic acid. The purified resin-free polymers were subjected to mass spectrometry (ZQ Waters) to confirm their composition and stored as a lyophilized powder at −20° C. Prior to being tested, fresh solutions were prepared in water, mixed by vortex, solubilized by ultrasound, centrifuged and then diluted in the appropriate medium.

In order to estimate the hydrophobicity of each polymer, the polymer was eluted with a linear gradient of acetonitrile (1% per minute) on an HPLC reversed-phase C18 column, and the percent of acetonitrile at which the polymer was eluted was used for hydrophobicity estimation (see, "ACN (%)" in Table 3 below).

Exemplary building units which were utilized in the synthesis described above are presented in Scheme 2 below and include: lysine and an ω-amino-fatty acid having m carbon atoms (Compound I).

Synthesis of exemplary polymers according to some embodiments of the present invention, which are comprised of lysine and Compound I, was performed by adding an Fmoc/Boc-protected lysine and an Fmoc-protected Compound I separately and sequentially to the resin according to conventional peptide solid phase synthesis protocols.

Scheme 2

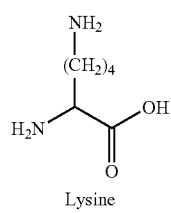

Lysine

-continued

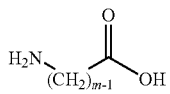

Compound I

Bacterial Strains:

Staphylococcus aureus ATCC 25923, Enterococcus faecalis (ATCC 29212), Escherichia coli ATCC 35218 and Vibrio cholerae serotype O1, Inaba biotype (ctxA+) was grown aerobically in Luria Bertani broth (LB, lysogeny broth), (Sigma Chemical Company, St. Louis, Mo., US) at 37° C. with shaking over night (16 hours). Cells were diluted to the specified concentration and subjected to the column.

pSMC2 in E. coli DH5alpha (GFP-expressing E. coli) was kindly provided by Dr. Kolter Harvard Medical School, USA [8].

Bacteria Capture Assay:

Various concentrations of bacteria in 500 μl luria bertani broth (LB) were shaken at room temperature in the presence of deprotected polymer-loaded beads (1.8 mg of polymer per sample) or protected polymer-loaded and unloaded beads as a control experiment in a centrifuge tube equipped with a 10 μm cutoff membrane (Whatman polypropylene mesh VectaSpin Micro). After 30 minutes incubation the samples were centrifuged at 21,000×g for 5 minutes to separate beads from unbound bacteria and further analyzed as follows.

As presented hereinabove, FIG. 1 presents a simplified illustration of an exemplary bacterial capturing device according to some embodiments of the present invention, composed on an exemplary polymer is linked to a solid support (resin bead), and a centrifuge filter tube is packed with such polymer-loaded resin beads (large dark spheres) which are incubated with a sample of bacteria cells (small light spheres), showing the capturing and concentration of the bacteria by the polymer-loaded resin beads after incubation and centrifugation (bottom-right tube), and the subsequent release of the bacteria from the polymer-loaded resin beads (bottom-left tube).

To assess bacterial binding to the beads, filtrates were subjected to serial 10 fold dilutions and plated on LB agar plates. Cell counts were determined using the drop plate method (three 20 μl drops onto LB agar plates) after overnight incubation at 37° C. For the viability study, resins were spread directly on LB agar plates and incubated similarly. For kinetic studies, resins were incubated with 1×10$^6$ CFU/ml E. coli in LB for up to 15 minutes and filtered after the indicated time periods then plated for CFU count.

The depletion assay was performed essentially as described above using successive incubation-filtration cycles that were repeated up to four times. During each cycle, the resin was incubated with 1×10$^6$ CFU/ml E. coli and filtered by centrifugation prior to being re-exposed to another portion of 1×10$^6$ CFU/ml E. coli cells.

For column filtration, the resin beads (10 mg) were packed in a glass pipette (topped by fiberglass to secure the resin). One liter of contaminated tap water (containing from about 10$^2$ to about 10$^5$ CFU of V. cholerae) was passed though the column at a flow rate of 50 ml per minute. Bacteria were eluted with a solution of 70% ethanol in water (1.8 ml), passed through the column and collected into a microtube for analysis by RT-PCR.

To assess release of viable (live) bacteria, the capture assay was performed as described above, then the polymer-bound bacteria were incubated for 15 minutes with different solutions, including lipopolysaccharide (LPS) of *E. coli O*111: B4, ammonium sulphate, ethanol, NaCl and ammonium sulphate:ethanol 1:1 mixture. The resulting filtrates were subjected to serial 10 fold dilutions and plated on LB agar plates for CFU count.

Bacterial Capture in Human Bodily Fluids:

For complex human bodily fluids, urine and whole blood sample were collected from healthy volunteers and placed in sterile vials (containing Na-citrate for blood), and were subsequently contaminated with *E. coli* and analyzed using the above mentioned assays.

For the whole blood assay, 10 ml of human blood contaminated with approximately 1 CFU/ml of *E. coli* (final bacterial content 10 CFUs per blood sample) as well as subsequent twofold dilutions, were added to 84 ml of the "Oxoid signal blood culture system" (Oxoid, UK). After 0, 2.5 or 4 hours incubation each sample was passed through a polymer-loaded column (as described above), eluted bacteria were analyzed by real-time-PCR (RT-PCR), as described hereinbelow.

In parallel, two other set of samples were prepared. In the first set (for RT-PCR analysis without the polymer-loaded system), blood samples were incubated for 0, 2.5, 4 and 6 hours, then DNA was extracted from an aliquot of 0.5 ml per sample using the QIAamp DNA Mini kit (Qiagen, UK) according to the manufacturer's instructions and analyzed by RT-PCR. In the second set (for analysis by the Oxoid standard method), blood samples were incubated for up to 24 hours and bacterial growth was determined under $CO_2$ pressure according to the manufacturer's instructions.

Visualization of Binding by Confocal Fluorescent Microscopy:

To visualize bacterial binding, resins were incubated with $1\times10^6$ GFP labeled *E. coli* KL2 for 30 minutes and then filtered by centrifugation as described above. Resin and filtrates were transferred to microscope slides and examined under a confocal fluorescent microscope (Nikon) using laser emission suitable for GFP (excitation at 485 nm emission at 535 nm) prior and after filtration.

To establish the viability of polymer-captured bacteria, samples of polymer-captured GFP-expressing bacteria were incubated for 15 minutes at room temperature in a solution of 1 ml propidium iodide (Invitrogen, USA) in PBS (final concentration 0.06 mM), and thereafter centrifuged/washed in PBS and examined under a confocal fluorescent microscope using emission suitable for GFP and propidium iodide (excitation at 490 nm emission at 620 nm).

For positive control, the polymer-bound bacteria were exposed to a solution of the antimicrobial peptide dermaseptin $K_4S4_{(1-16)}$ at 12.5 μM (4 times the MIC value) in PBS for 15 minutes, as described previously [9] then stained as described herein.

DNA Preparation for Real-Time PCR (RT-PCR):

Bacterial cells were eluted from the resin with 1.8 ml of 70% ethanol suspension followed by addition of 59.4 μl of 3

M Na-Acetate, incubated for one minute in liquid nitrogen (or for 20 minutes at −80° C.) and centrifuged (18,000 g) for 15 minutes. The pellet was suspended in 20 µl dilute TE buffer (1 mM Tris in 0.1 EDTA, pH 8.0) and DNA submitted to real-time PCR analysis as detailed below.

Bacterial Binding Assays Using Real-Time SPR Technology:

Purified resin-free polymers were immobilized onto the CM5 sensor chip (BIAcore, Uppsala, Sweden) via the terminal carboxyl group using 2-(2-pyridinyldithio)ethaneamine (PDEA). Carboxyl activation was achieved as follows. Morpholino-ethanesulfonic acid (MES buffer, 0.1 ml of 0.1 M) at pH 5.0 was used to solubilize 0.1 mg of the polymer. The solution was mixed with PDEA to final concentration of 22 mM and ethyl-3-(3-dimethylaminopropyl)-carbodiimide (EDC) to final concentration of 13 mM, incubated for 1 hour on ice and then placed in a dialysis tube (floating in buffer) to remove the excess reagents. In parallel, a 1:1 solution (20 µl) of EDC (0.4 M 1-ethyl-3-(3-dimethylaminopropyl)-carbodiimide in water):NHS (0.1 M N-hydroxysuccinimide in water) was injected at a flow rate of 10 µl/minute, to activate the chip surface. Thereafter, 30 µl of a solution of cystamine was injected to introduce a disulfide group. The disulfides bonds were reduced with 30 µl DTE (0.1 M dithioerythritol or dithiothreitol in 0.1 M sodium borate pH 8.5). Subsequently, the dialyzed polymer solution (60 µl containing 10 µg) was injected to immobilizing the polymer while excess reactive groups on the chip were deactivated using a 40 µl solution of PDEA (20 mM of 2-(2-pyridinyldithio)ethaneamine and 1 M NaCl in 0.1 M sodium acetate pH 4.0).

Bacterial binding to the polymer was determined by surface plasmon resonance (SPR) using the optical biosensor system BIAcore 2000 (BIAcore, Uppsala, Sweden). The experimental procedure and data interpretation were performed essentially as described previously [10]. Briefly, to monitoring bacterial binding, 100 µl of E. coli in saline (at the concentrations of $10^3$, $10^4$, $10^5$ and $10^6$ CFU/ml) were injected over the polymer-coated chip at a flow rate of 20 µl/minutes and collected by an integrated sample collector after each run. Aliquots from each run were platted on LB agar plates for enumeration after overnight incubation at 37° C. Bound bacteria were estimated by comparing the CFU count before and after each run.

Bacterial (V. cholerae) Binding Assays Using Real-Time PCR Technology:

Universal 16S rRNA primers were selected from a conserved bacterial region to give a PCR product of 180 base-pairs; a suitable length product for real time PCR. Primers' sequences were:

```
UNI-F
5'-AGGATTAGATACCCTGGTAGT-3';    (SEQ ID NO: 1)
and

UNI-R
5'-CGAATTAAACCACATGCTCCA-3'.    (SEQ ID NO: 2)
```

Outer membrane protein W (OmpW) family is a family of evolutionarily related proteins from the outer bacterial membrane from a variety of bacterial species. This protein may form the receptor for S4 colicins in E. coli. Colicins, or bacteriocins, are proteinaceous toxins produced by bacteria to inhibit the growth of similar or closely related bacterial strain(s).

OmpW PCR primers were designed on the basis of ompW sequence, uniquely present in V. cholerae, to generate amplicons of 588 base-pairs from all V. cholerae strains [11].

The species-specific primers were:

```
OmpW 1-5-F
5'-CACCAAGAAGGTGACTTTATTGTG-3';   (SEQ ID NO: 3)
and

OmpW 1-5-R
5'-GGAAAGTCGAATTAGCTTCACC-3'.     (SEQ ID NO: 4)
```

Primers for cholera toxin gene type A (ctxA) were selected to gives a PCR product of 301 base-pairs [12].

Primers' sequences were:

```
ctrA-F
5'-CTCAGACGGGATTTGTTAGGCACG-3';   (SEQ ID NO: 5)
and ctrA-R
5'-TCTATCTCTGTAGCCCCTATTACG-3'.   (SEQ ID NO: 6)
```

Primers for pepD gene were selected to gives a PCR product of 318 base-pairs (the expected product size is according to the E. coli K-12 complete genome, GenBank accession U00096).

Primers' sequences were:

```
pepD-F
5'-GGA GAT AAT TGA GAC AGT TCA G-3';  (SEQ ID NO: 7)
and pepD-R
5'-ATG TCC CAG GTG ACG ATG-3'.        (SEQ ID NO: 8)
```

Real-time PCR reactions were carried out in a Rotor-Gene™ 3000 (Corbett research, Sydney, Australia). PCR was performed by using 12.5 µl ABsolute™ QPCR SYBR® Green Mix (ABgene), 2.5 µM of each of the forward and reverse primers, 5 µl of extracted bacterial genomic DNA (0.03-3 ng/reaction) and water to make up to 25 µl.

Thermal cycling conditions were as follows. Amplification starts with a step of enzyme activation and initial denaturation at 95° C. for 15 minutes, followed by 40 cycles consisted of denaturation at 95° C. for 10 seconds, annealing at 60° C. (53° C. for pepD) for 15 seconds and extension at 72° C. for 20 seconds.

Results

Polymer Preparation:

Several representative series of polymers according to some embodiments of the present invention, which are substantially comprised of a plurality of lysine residues, and ω-amino-fatty acid residues and fatty acid residues as hydrophobic moieties, were prepared according to the general procedure described above and in U.S. Patent Application Nos. 2006/0074021 and 2007/0032428, WO 2006/035431 and U.S. Provisional Patent Application Nos. 60/924,087 and 60/924,088, each being incorporated herein in its entirety. These polymers are presented in Table 3 below.

These exemplary polymers are referred to in this section according to the following formula:

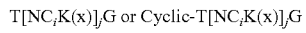

T[NC$_i$K(x)]$_j$G or Cyclic-T[NC$_i$K(x)]$_j$G

In this formula, the prefix "Cyclic-" denotes a cyclic polymer; NC$_i$ denotes an ω-amino-fatty acid residue (an exemplary hydrophobic moiety according to the present invention, represented by D$_1$ . . . Dn in the general formulae I and II described herein), whereby i denotes the number of carbon atoms in the fatty acid residue; K denotes a lysine residue (an exemplary amino acid residue according to the present invention, denoted as A$_1$ . . . An in the general Formulae I and II described herein, such that [NC$_i$K(x)] denotes a residue of an ω-amino-fatty acid-lysine conjugate (denoted as [A$_1$-Z$_1$-D$_1$] [An-Zn-Dn] in the general Formulae I and II described herein) wherein (x) denotes the type of amine group in the amino acid used for conjugation with one end of the hydrophobic moiety (e.g., the ω-amino-fatty acid), whereby when the denotation (x) is absent, it is meant that conjugation is effected via the N-alpha of the lysine residue and when (x) is (ε) it is meant that conjugation is effected via the epsilon amine of the lysine residue; j denotes the number of the repeating units of a specific conjugate in the polymer (corresponding to n in the general Formulae I and II described herein); and T and G each independently denotes either a hydrogen (no denotation), a lysine residue (denoted K), an ω-amino-fatty acid residue (denoted NC$_i$), a fatty acid residue (denoted C$_i$), an ω-amino-fatty acid-lysine conjugate residue (denoted NC$_i$K), a fluorenylmethyloxycarbonyl residue (denoted Fmoc), a benzyl residue (denoted Bz), a tert-butylcarbonyl residue (denoted t-Boc or Boc), an amine group (typically forming an amide at the C-terminus and denoted NH$_2$), and free acid residue (for the C-terminus no denotation), an alcohol residue, and any combination thereof (all corresponding to X and Y in the general Formula I described herein).

Thus, for example, a polymer according to embodiments of the present invention which is referred to herein as C$_{12}$K(NC$_8$K)$_7$NH$_2$, corresponds to a polymer having the general Formula I described hereinabove, wherein: X is a residue of a conjugate of a fatty acid having 12 carbon atoms (lauric acid) and lysine; n is 6; A$_1$ . . . A$_6$ are each a lysine residue; D$_1$ . . . D$_7$ are all residues of an ω-amino-fatty acid having 8 carbon atoms (8-amino-caprylic acid); Z$_1$ . . . Z$_7$ and W$_0$-W$_7$ are all peptide bonds; and Y is an amine. For clarity, the chemical structure of C$_{12}$K(NC$_8$K)$_7$NH$_2$ is presented in Scheme 3 below:

Scheme 3

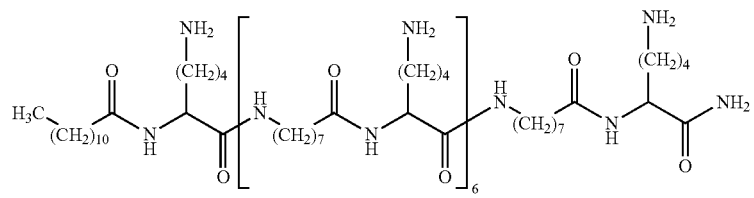

For another example, a polymer according to the present embodiments which is referred to herein as C$_{12}$K(ε)NC$_{12}$K(ε)NH$_2$, corresponds to a polymer having the general Formula I described hereinabove, wherein: X is a residue of a conjugate of an ω-amino-fatty acid having 12 carbon atoms (12-amino-lauric acid) and lysine; n is 61 hence not denoted; A$_1$ . . . A$_6$ A$_2$ are each a lysine residue, both conjugated via the epsilon amine hence denoted K(ε); D$_1$ . . . D$_7$ are all is a residues of an ω-amino-fatty acid having 12 carbon atoms (12-amino-lauric acid); Z$_1$ . . . Z$_7$ Z$_2$ and W$_0$-W$_{71}$ are all peptide bonds; and Y is an amine. For clarity, the chemical structure of C$_{12}$K(ε)NC$_{12}$K(ε)NH$_2$ is presented in Scheme 4 below:

Scheme 4

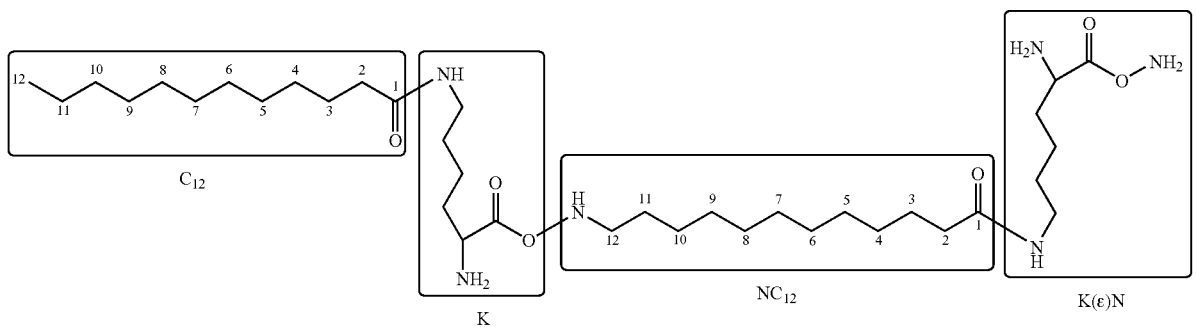

Table 3 below presents the exemplary polymers according to some embodiments of the present invention, which were tested for their bacterial capturing capacity. It is noted herein that the polymers are presented in formulae and general formulae as resin-free polymers (not linked to any matrix or support), while the resin-bound polymers are typically linked to the resin via a terminal functional group, such as, for example, the C-terminal amide group.

Bacterial Capture:

Bacterial binding (capturing) by exemplary polymers was assessed and then characterized under both stationary incubation- and continuous-flow conditions according to the procedures presented above, and the results of these assays are presented hereinbelow.

An exemplary polymer, according to some embodiments of the present invention, $C_{12}K(NC_8K)_7NH_2$ displayed potent bactericidal properties [9], and thus polystyrene-based resin beads carrying this compound as well as a series of other polymers (see, Table 3 hereinbelow) were initially screened for bacterial binding abilities using the capture assay.

Table 3 below presents exemplary polymers according to some embodiments of the present invention and their physical properties (charge and hydrophobicity), as well as their antimicrobial activity and their bacteria capturing capacity when bound to a solid support resin, wherein:

"Q" represents the overall molecular charge at physiological pH (column 3 in Table 3);

"ACN (%)" represents the percent of acetonitrile in the RP-HPLC gradient mobile phase at which the polymer was eluted and which corresponds to the estimated hydrophobicity of the polymer (column 4 in Table 3);

"MIC (μM)" represents the minimal inhibitory concentration of each tested polymer in μM for each bacterial strain, measured as described previously [13] (columns 5-8 in Table 3); For bacterial strains, "Ec" represents $E.$ $coli$; "Pa" represents $P.$ $aeruginosa$; "Sa" represents $S.$ $aureus$; and "Bc" represents $B.$ $cereus$; and "Bound $E.$ $coli$ (CFU/mg resin)" represents the capturing capacity of bacterial binding per one milligram of polymer-loaded resin beads as assessed after 30 minutes incubation using the capture assay as presented herein (column 9 in Table 3).

the resin-free polymer, reflecting the importance of the hydrophobicity characteristics. Indeed, replacing the aminocaprylic backbone with aminolauryl residues generated the polymer $K(NC_{12}K)_7NH_2$ that was virtually devoid of antibacterial activity (MIC more than 50 μM) but displayed a 1000 fold higher bacterial binding capabilities as compared to $C_{12}K(NC_8K)_7NH_2$. This polymer, namely $K(NC_{12}K)_7NH_2$, was used for further experimentation in the protected and deprotected forms, namely where the amine of the side chain of the terminal lysine is protected or unprotected by a Boc group.

FIG. 2 summarizes the results of the bacterial capturing using $K(NC_{12}K)_7NH_2$ as an exemplary bead-bound polymer according to some embodiments of the present invention, wherein the incubation assays, in which the bacterial binding was assessed initially by CFU count of the resulting filtrates, were followed by depletion assays which were performed in order to verify the binding capacity. These experiments were repeated using different bacteria strains in order to determine specificity. The error-bars represent a standard deviation from the mean, while the lack thereof indicates consistency, and stars indicate negative cultures (i.e., less than 50 CFU/ml).

Figure 2A:
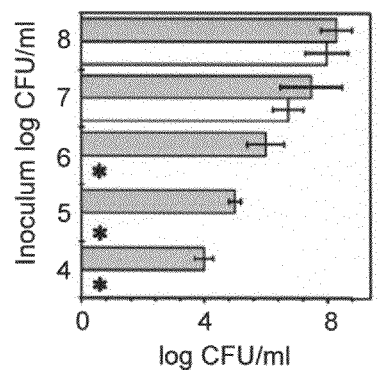

FIG. 2a is a comparative bar-plot, showing the CFU count of the un-captured $E.$ $coli$ cells found in the filtrates after 30 minutes incubation at the specified concentrations ($10^4$-$10^8$ CFU/ml) with 1.8 mg of Boc-protected (grey) and unprotected (white) $K(NC_{12}K)_7NH_2$ polymer, whereas the actual count was performed by plating the filtrates on LB agar for enumeration.

As can be seen in FIG. 2a, complete (100%) binding was observed with filtrates resulting from incubation with up to $10^6$ CFU/ml, but filtrates from the higher inoculums of $10^7$ and $10^8$ CFU/ml displayed progressively lower binding proportions, reflecting gradual saturation of the available polymers. No bacterial binding was observed for polymer-free beads (data not shown), and for polymer-loaded beads wherein the lysine side chains were still protected by a Boc group. The fact that bacterial binding occurred only with the deprotected form of the polymer demonstrated that the process was specifically related to the polymer's properties.

Figure 2C:
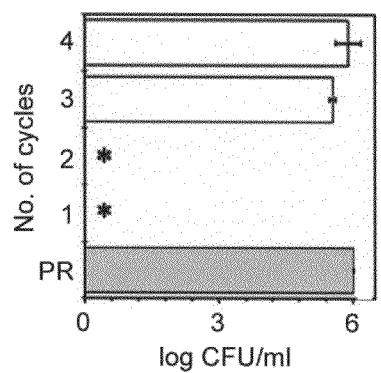
Figure 2B:
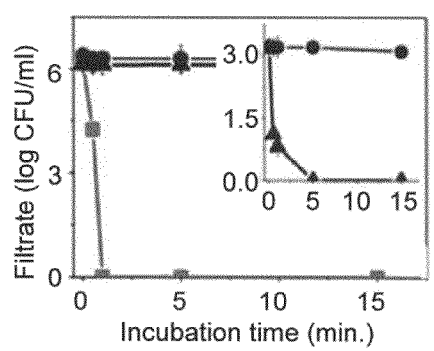

FIG. 2b is a comparative plot showing the time dependence of $E.$ $coli$ capture as assessed by CFU count determined for

TABLE 3

| Polymer | No. of residues | Q | ACN (%) | MIC (μM) | | | | Bound $E.$ $coli$ (CFU/mg resin) |
| --- | --- | --- | --- | --- | --- | --- | --- | --- |
| | | | | Ec | Pa | Sa | Bc | |
| $C_{12}K(NC_8K)_7NH_2$ | 16 | 8 | 47.5 | 3.1 | 6.2 | 50 | 12.5 | $1 \pm 0.5 \times 10^3$ |
| $K_8NH_2$ | 8 | 9 | 20 | >50 | >50 | >50 | >50 | $9 \pm 1 \times 10^2$ |
| $K_{15}NH_2$ | 15 | 16 | 22 | >50 | >50 | >50 | >50 | $1 \pm 0.6 \times 10^3$ |
| $K(NC_8K)_7NH_2$ | 15 | 9 | 34 | >50 | >50 | >50 | >50 | $2 \pm 0.6 \times 10^2$ |
| $K(NC_{12}K)_7NH_2$ | 15 | 9 | 50 | >50 | >50 | >50 | >50 | $1 \pm 0.3 \times 10^6$ |

As can be seen in Table 3, when exposed to $E.$ $coli$, polymer-loaded resin beads bearing the $C_{12}K(NC_8K)_7NH_2$ polymer were able to capture bacteria in an amount of approximately $10^3$ CFUs. As can further be seen in Table 3, a polymer lacking all the acyl residues, namely the polylysine octamer $K_8$, had no significant effect including when the polymer was elongated to include 15 residues as in $K_{15}$, supporting the notion that bacterial capture is partly based on electrostatic interactions.

Interestingly however, the polymer $K(NC_8K)_7NH_2$, lacking only the N-terminal lauryl moiety compared to the $C_{12}K(NC_8K)_7NH_2$ polymer, exhibited a reduced amount of captured bacteria as well as reduced antibacterial properties of filtrates after incubation at the specified time periods in the presence of 1.8 mg of deprotected (red rectangles) and Boc-protected (green circles) $K(NC_{12}K)_7NH_2$-loaded beads, and $K_{15}NH_2$-loaded beads (blue triangles) were used as control, whereas the insert shows a low concentration experiment comparing $K_{15}NH_2$-loaded beads (blue triangles) and the bare resin as control (green circles).

As can be seen in FIG. 2b, bacterial binding was spontaneous and rapid as assessed by these kinetic studies wherein $E.$ $coli$ were incubated with the beads-bound polymer $K(NC_{12}K)_7NH_2$ for increasing time periods followed by CFU counts performed after spin-filtration. As can be seen in FIG. 2b, bacterial counts dropped by two log units (from $10^6$ to $10^4$ CFU/ml) after 30 seconds incubation, whereas negative cultures were obtained after 60 seconds incubation and thereafter. No bacterial capturing was recorded on the control resin beads even after 30 minutes incubation.

FIG. 2c is a bar-plot showing the binding capacity of E. coli ($1\times10^6$ to CFU/ml/cycle) to 1.8 mg of unprotected $K(NC_{12}K)_7NH_2$ polymer as determined by repeated incubation/filtration cycles (depletion assays), wherein after each cycle, the filtrate was plated on LB agar for enumeration, and "PR" represents a one-cycle control experiment performed with a 1.8 mg Boc-protected polymer.

As can be seen in FIG. 2c, the binding capacity of the exemplary $K(NC_{12}K)_7NH_2$ polymer was confirmed with a depletion experiment using consecutive incubation/filtration cycles, wherein negative cultures were obtained with filtrates resulting from the first two cycles, and whereas the third and fourth cycles yielded $7\times10^5$ and $1\times10^6$ CFU/ml, respectively, indicating a gradual saturation of the available binding sites in the resin-bound polymer. From the combined data presented in FIGS. 2a and 2c, it can be estimated that each milligram of beads-bound $K(NC_{12}K)_7NH_2$ polymer (approximately 300 beads) bind slightly more than $1\times10^6$ CFU of E. coli.

Figure 2D:
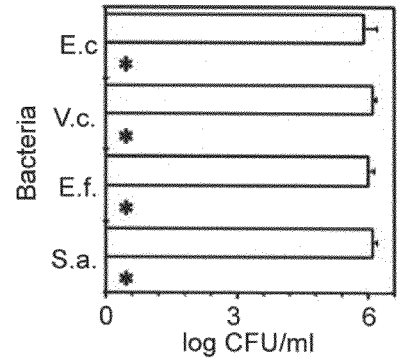

FIG. 2d is a comparative bar-plot, showing the bacterial binding specificity of the exemplary $K(NC_{12}K)_7NH_2$ polymer versus a variety of bacterial strains as determined for filtrates after 30 minutes incubation in the presence of 1.8 mg of the Boc-protected (white) and unprotected beads-bound polymer with $1\times10^6$ CFU/ml of each of E. coli (E.c.), V. cholerae (V.c.), E. faecalis (E.f.) and S. aureus (S.a.).

As can be seen in FIG. 2d, bacterial binding to the $K(NC_{12}K)_7NH_2$ polymer was not species-specific with respect to any given bacterial strain as adhesion was essentially similar when using typical Gram-negative (E. coli and V. cholerae) or Gram-positive (E. faecalis and S. aureus) bacteria.

FIG. 3 is a comparative plot showing the viability of bacteria after elution from $K(NC_{12}K)_7NH_2$-loaded resin beads using LPS (X-axis denotes the concentration in ng/ml, and data marked in green rectangles); 10% ammonium sulphate: ethanol solution in water (concentration in % ethanol v/v and data marked in pink circles); ethanol in water (concentration in % ethanol v/v and data marked in yellow triangles). Other treatments such as ammonium sulfate and NaCl did not release live bacteria (data not presented).

Visualization of Binding by Confocal Fluorescent Microscopy:

Bacterial binding was visualized using green fluorescent protein (GFP) expressing E. coli as analyzed by fluorescence confocal microscopy.

FIG. 4 presents a series of fluorescence confocal microscopy images of GFP expressing E. coli, wherein the bacteria was detected in the surrounding medium after failing to bind to the exemplary Boc-protected $K(NC_{12}K)_7NH_2$-loaded resin beads control sample (FIG. 4a), but clearly interacted with the deprotected $K(NC_{12}K)_7NH_2$-loaded resin beads (FIG. 4b), indicating that bacterial adhesion occurs during the incubation and prior to filtration, and further showing that the bacteria remained attached to the deprotected polymer sample after the filtration step (FIG. 4c), which is consistent with high binding affinity, and that 5 minutes treatment with 70% ethanol resulted in dissociation of the polymer-captured bacteria (FIG. 4d) suggesting that the beads-bound polymers can be recycled readily as further demonstrated hereinbelow.

Figures 5A, 5B, 5C, 5D:
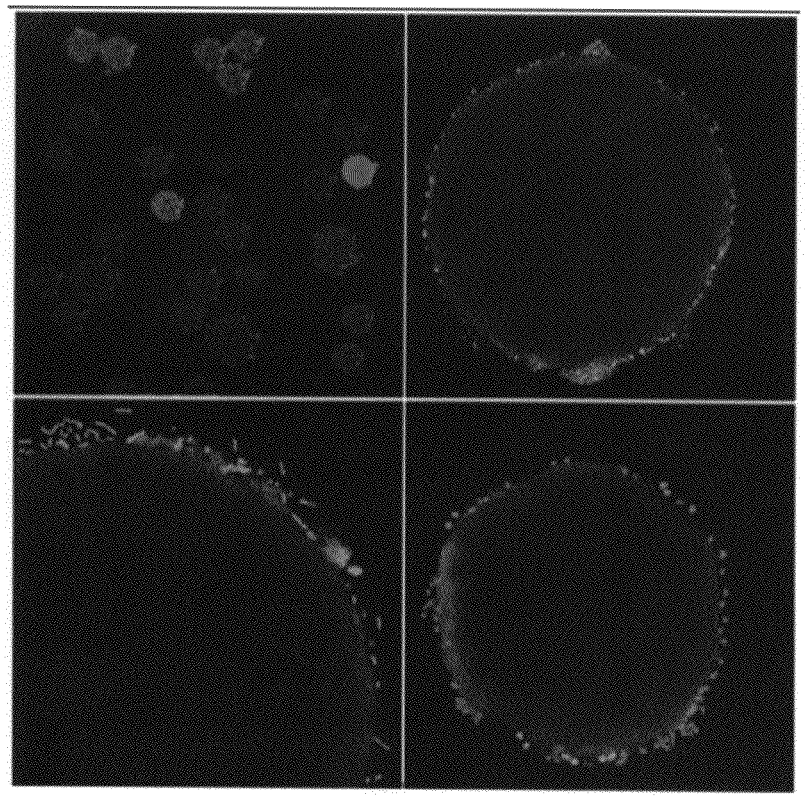

FIG. 5 presents a series of fluorescence confocal microscopy images $K(NC_{12}K)_7NH_2$-captured bacteria after treatment with propidium iodide, wherein the green and red colors indicate live and dead bacteria, respectively (FIG. 5A is a low magnification image and FIGS. 5B-D are zoomed images), whereas FIG. 5C is an image recorded before treatment with the antimicrobial peptide dermaseptin and FIG. 5D is an image recorded after treatment with dermaseptin.

As can be seen in FIG. 5, most polymer-captured bacteria were alive, since most have excluded the dye propidium iodide. The fraction of dead bacteria (colored red) did not exceed that of a control suspension (up to 12% as assessed by BacLight LIVE/DEAD kit). As can be seen in FIG. 5D, fraction of dead bacteria significantly increased upon exposure to the AMP dermaseptin, known for its rapid bactericidal properties.

The non-cytotoxicity of the beads-bound polymers was assessed by the viability of the polymer-captured bacteria. E. coli was incubated with beads-bound polymers ($10^6$ CFU/ml/mg resin), and after filtration, samples of the resins and the filtrates were plated on LB-agar individually.

FIG. 6 presents a series of images of LB-agar plates, showing the viability of the captured E. coli cells ($1\times10^6$ CFU/ml) which were incubated for 30 minutes with deprotected (FIGS. 6A1 and 6A2) and Boc-protected (FIGS. 6B1 and 6B2) $K(NC_{12}K)_7NH_2$-loaded resin beads, wherein FIGS. 6A1 and 6B1 show the plates of the plated filtrates and FIGS. 6A2 and 6B2 show the plates of filtered and plated beads.

As can be seen in FIG. 6, the filtrate obtained from the deprotected polymer sample did not contain viable bacteria (FIG. 6A1) while the beads-bound bacteria of that sample remained alive (FIG. 6A2). As can further be seen in FIG. 6, the filtrate obtained from the protected polymer sample contained viable bacteria (FIG. 6B1), while the filtered beads of that sample which were plated after filtration contained no viable bacteria (FIG. 6B2).

Figure 7:
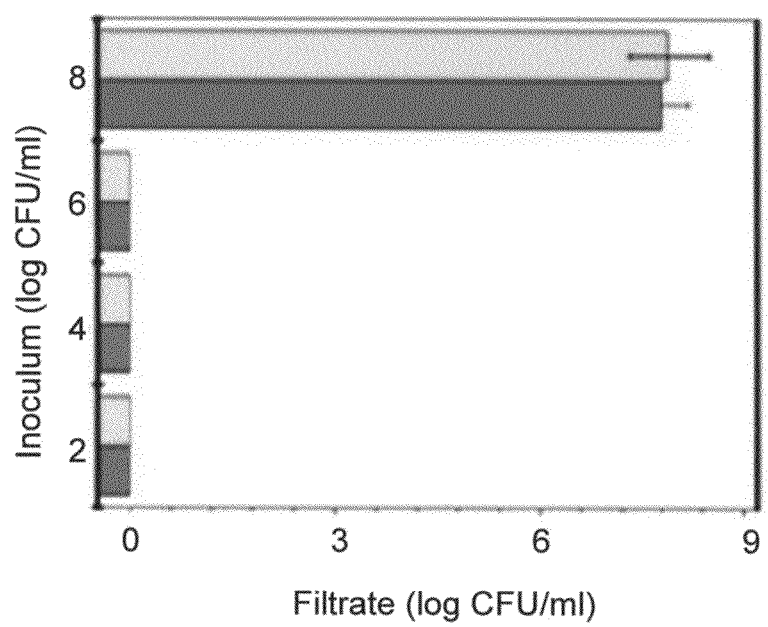
FIG. 7 is a comparative bar-plot, showing the bacterial capture effected by the exemplary $K(NC_{12}K)_7NH_2$-loaded resin beads in human urine (yellow bars) and whole human blood (red bars) inoculated with *E. coli*.

Bacterial Capture in Human Bodily Fluids:

FIG. 7 is a comparative bar-plot, showing the bacterial capture effected by the exemplary $K(NC_{12}K)_7NH_2$-loaded resin beads in human urine (yellow bars) and whole human blood (red bars) inoculated with E. coli and assessed as described hereinabove.

As can be seen in FIG. 7, $K(NC_{12}K)_7NH_2$-loaded resin beads were also able to capture bacteria in human urine and whole human blood, respectively.

The bacterial capturing system according to some embodiments of the present invention, was used to tackle a typical problem that is still currently intractable with the best alternatives as represented by the time required for detection/identification of bacterial contaminations in whole blood. The standard method currently used in hospitals (such as the "Oxoid signal blood culture system", Oxoid, UK) requires 24 hours to 7 days sample incubation, a time delay that may be critical in various clinical situations such as in the emergency room. The experiment presented herein, using an exemplary bacteria-capturing polymer-loaded column combined with RT-PCR was shown to speed up the process to a significant extent, and the results are presented in Table 4 hereinbelow.

Table 4 presents the results of the bacterial contamination detection tests in terms of feasibility of detection in 10 ml of human blood, comparing the time of incubation in hours needed to obtain a positive detection after incubation in "Oxoid signal blood culture medium" using three detection methods: a standard "Oxoid signal blood culture system" method (Oxoid, UK), a standard RT-PCR method and a $K(NC_{12}K)_7NH_2$-loaded resin beads packed column combined with RT-PCR. The plus signs (+) designate positive bacterial detection either by $CO_2$ pressure for the standard method or by RT-PCR products for the alternative methods, the minus signs (−) designate insufficient bacteria levels which were below level of detection, and "nd" denotes results not determined.

TABLE 4

| Test method | Inoculum (CFU/sample) | Incubation time (in hours) | | | | | | |
|---|---|---|---|---|---|---|---|---|
| | | 0 | 2.5 | 4 | 6 | 12 | 18 | 24 |
| Standard "Oxoid signal blood culture system" (Oxoid, UK) | 1.25 | − | − | − | − | − | − | + |
| | 2.5 | − | − | − | − | − | − | + |
| | 5 | − | − | − | − | − | − | + |
| | 10 | − | − | − | − | − | + | + |
| Real time-PCR | 1.25 | − | − | − | + | nd | nd | nd |
| | 2.5 | − | − | − | + | nd | nd | nd |
| | 5 | − | − | − | + | nd | nd | nd |
| | 10 | − | − | − | + | nd | nd | nd |
| $K(NC_{12}K)_7NH_2$-loaded column combined with RT-PCR | 1.25 | − | − | + | nd | nd | nd | nd |
| | 2.5 | − | + | + | nd | nd | nd | nd |
| | 5 | − | + | + | nd | nd | nd | nd |
| | 10 | + | + | + | nd | nd | nd | nd |

As can be seen in Table 4, combination of a $K(NC_{12}K)_7NH_2$-loaded resin beads packed column combined with RT-PCR analysis produced results for all tested concentrations after only 4 hours of incubation, compared with 6 and 24 hours needed for RT-PCR and the standard Oxoid method, respectively. Moreover, only the polymer-based method succeeded in detecting bacteria at lower incubation times. Thus, 2.5 hours incubation were required to detect inoculums greater or equal to 2.5 CFU, while no incubation period was necessary to detect bacterial contamination equivalent to 10 CFUs.

Bacterial Binding Assays Using Real-Time SPR Technology:

Bacterial binding under continuous flow conditions was assessed using surface plasmon resonance (SPR) technology, designed to corroborate the binding affinity and the potential usefulness of the concept of bacteria-capturing polymers.

For real-time monitoring of bacterial capture the present inventors have developed a model system based on the SPR technology that normally enables binding measurements between immobilized receptor molecules and soluble ligands [10, 14]. SPR-affinity measurements using liposomes as a model for mimicking bacterial membranes, showed high affinity binding of the resin-free polymers to the model membrane, with $K_{app}$ ranging from $10^4$ to $10^7$ M$^{-1}$ [5]. In the example presented herein, the polymer was immobilized onto the sensor chip and bacteria were injected over the polymer-bound surface and their binding monitored in real-time. Each experimental run included injection of a bacterial suspension of known concentration during 600 seconds, followed immediately by a PBS wash step. The measurements presented herein using live bacterial cells could not be presented in terms of molar concentration; however the SPR response indicated similar affinity values of the chip-immobilized polymers to intact bacterial cells compared to the affinity measured for resin-free polymers.

Figure 8A:
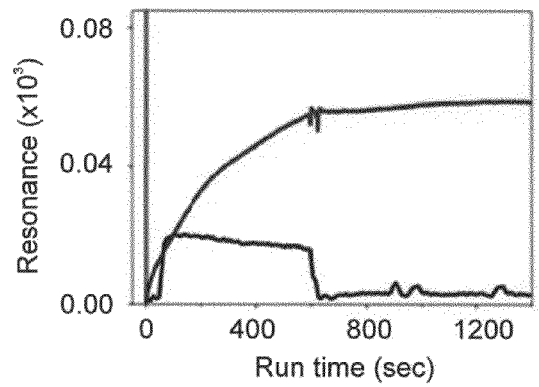
FIGS. 8A-C present the results of the real-time surface plasmon resonance (SPR) experiment, showing the association/dissociation sensorgram obtained for $10^6$ CFU/ml suspensions of *E. coli* using $K_{15}NH_2$ (marked in blue in FIG. 8A), $K(NC_{12}K)_7NH_2$ (marked in red in FIGS. 8A and 8B) and Boc-protected $K(NC_{12}K)_7NH_2$ (marked in black in FIG. 8A) coated chips, and showing the dose-dependence of *E. coli* binding to $K(NC_{12}K)_7NH_2$-coated chip for suspensions containing $10^2$, $10^3$, $10^4$, $10^5$ and $10^6$ CFU/ml (colored respectively in blue, cyan, black, green and red in FIGS. 8B and 8C) and the CFU counts (FIG. 8C) obtained from each run presented in FIG. 8B (colors indication is as in FIG. 8B)
Figure 8B:
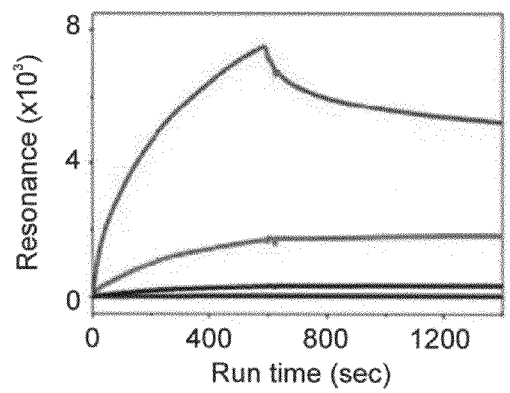
Figure 8C:
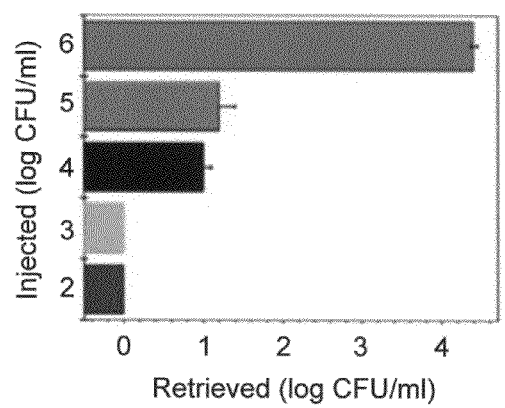
Figure 9A:
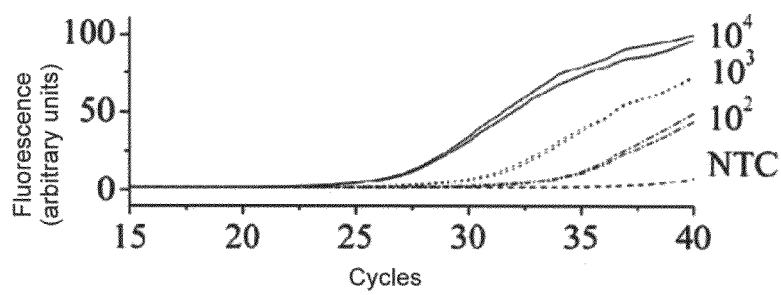
FIGS. 9A-C present the results of the real-time PCR amplification used for the detection of the pathogenic *V. cholerae* O1 bacteria in saline using a column packed with $K(NC_{12}K)_7$-$NH_2$-bound beads to effect bacterial capture and concentration, showing the relative SYBR Green (a nucleic acid staining dye) fluorescence development as a function of the number of cycles of samples amplification using 16S universal primers (UNI) for detection of bacterial cells (FIG. 9A), *V. cholerae* O1 specific primers, ompW (FIG. 9B) and ctx (FIG. 9C) locus primers, and using an NTC primer as a non template control.
Figure 9B:
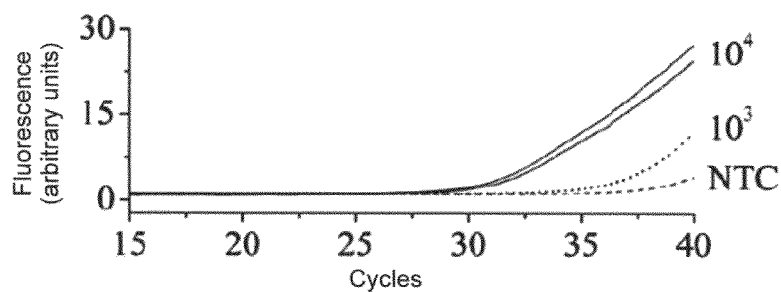
Figure 9C:
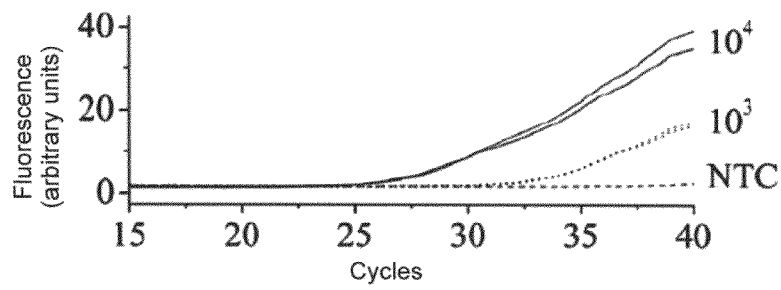

FIG. 8 presents the results for the assessment of bacterial binding using SPR technology, showing the association/dissociation sensorgrams obtained for $10^6$ CFU/ml suspensions of *E. coli* using $K_{15}NH_2$ (marked in blue in FIG. 8A), unprotected $K(NC_{12}K)_7NH_2$ (marked in red in FIGS. 8A and 8B) and Boc-protected $K(NC_{12}K)_7NH_2$ (marked in black in FIG. 8A) coated chips, and showing the dose-dependence of *E. coli* binding to $K(NC_{12}K)_7NH_2$-coated chip for suspensions containing $10^2$, $10^3$, $10^4$, $10^5$ and $10^6$ CFU/ml (colored respectively in blue, cyan, black, green and red in FIGS. 8B and 8C) and the CFU counts (FIG. 8C) obtained from each run presented in FIG. 8B (colors indication is as in FIG. 8B). It is noted herein that the control experiments including bacteria injected over non-coated chip or saline injected over $K(NC_{12}K)_7NH_2$ or $K_{15}NH_2$ coated chips, yielded a negligible resonance signal (less than 10% of that observed with Boc-protected polymer shown in FIG. 8A.

As can be seen in FIGS. 8A and 8B, the protected polymer did not retain bacteria while $K_{15}NH_2$ coated chip was more than 100-fold less efficient than the $K(NC_{12}K)_7NH_2$-coated chip. Thus, whereas bacteria accumulated/associated rapidly on the $K(NC_{12}K)_7NH_2$-coated chip surface throughout the injection stage, no bacterial release/dissociation was detected at the wash stage with the exception of the highest concentration tested ($10^6$ CFU/ml) where the wash step displayed some dissociation. It is noted herein that this observation is likely to reflect saturation of the binding sites on the chip.

As can be seen in FIG. 8C, the SPR data was validated by plating each of injected samples, collected at its exit from the chip compartment, for CFU count. As can be deduced from FIG. 8C, the fact that bacteria were not detected up to $10^3$ CFU/ml and only about 10 CFU values were counted when $10^4$ or $10^5$ CFU/ml were injected, supports the assumption that nearly 100% bacterial binding was obtained at these conditions. Accordingly, the fact that about 90% binding was obtained when injecting $10^6$ CFU/ml suggests that the chip maximal binding capacity was achieved at $10^5$ CFU/ml which is consistent with the sensorgams, presented in FIGS. 8A and 8B.

This interpretation assumes that the sole mode of bacterial interaction with the chip is a monolayer type due to the continuous flow and the chip cell volume, unlike bacterial capture by beads which may include multiple layers (see, FIG. 5C).

Bacterial Binding Assays Using Real-Time PCR Technology:

To further asses the capturing and concentrating capabilities of the polymers according to embodiments of the present invention in a continuous flow system, the present inventors have elected to mimic a diagnostic situation seeking detection of the pathogenic *V. cholerae* bacteria.

To that end, one liter of sterile saline was inoculated with $10^2$-$10^4$ cells of *V. cholerae* and passed through a column packed polymer-bound beads. Polymer-captured bacteria were eluted from the column with 1.8 ml ethanol, which was parsed into aliquots and subjected to DNA analysis by real-time PCR.

FIG. 9 presents the results of the real-time PCR amplification used for the detection of the pathogenic *V. cholerae* O1 bacteria in saline using a column packed with $K(NC_{12}K)_7NH_2$-bound beads to effect bacterial capture and concentration, showing the relative SYBR Green (a nucleic acid staining dye) fluorescence development as a function of the number of cycles of samples amplification using 16S universal primers (UNI) for detection of bacterial cells (FIG. 9A), *V. cholerae* specific primers, ompW (FIG. 9B) and ctx (FIG. 9C) locus primers, and using an NTC primer as a non template control.

As can be seen in FIG. 9, positive identification was obtained with a concentration as low as 10 CFU/100 ml saline using universal 16S RNA primers (FIG. 9A), whereas positive identification was obtained at slightly higher bacterial concentration (100 CFU/100 ml) when using specific primers (ompW and ctx) for *V. cholerae* O1 (FIG. 9B and FIG. 9C, respectively).

To simulate sensitive identification of pathogenic bacteria in drinking water containing a background level of natural microflora, 1 liter of tap water was contaminated with low concentrations of *V. cholerae*.

Figure 10A:
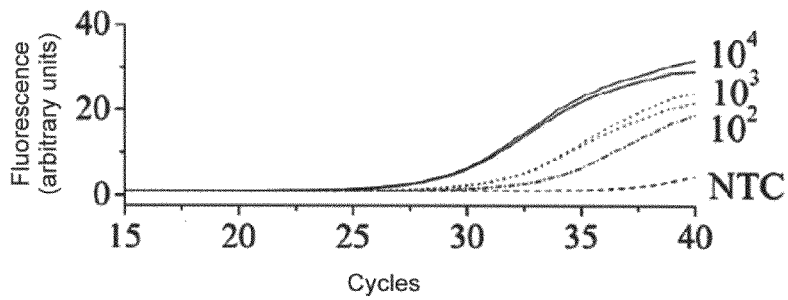
FIGS. 10A-C presents the results of the real-time PCR amplification used for the detection of *V. cholerae* in tap water inoculated with $10^2$-$10^4$ *V. cholerae* O1 cells after its concentration using a column packed with polymer-bound beads at similar experimental conditions as described in FIG. 9, showing the relative SYBR Green fluorescence development obtained for 1 liter tap water as a function of the number of cycles of sample amplification using ompW (FIG. 10A) and ctx (FIG. 10B) locus primers, and the results obtained for a 10 liters tap water sample inoculated with $10^3$ *V. cholerae* O1 cells (10 CFU/100 ml) and amplified with ctx locus primers (FIG. 10C), and using an NTC primer as a non template control.
Figure 10B:
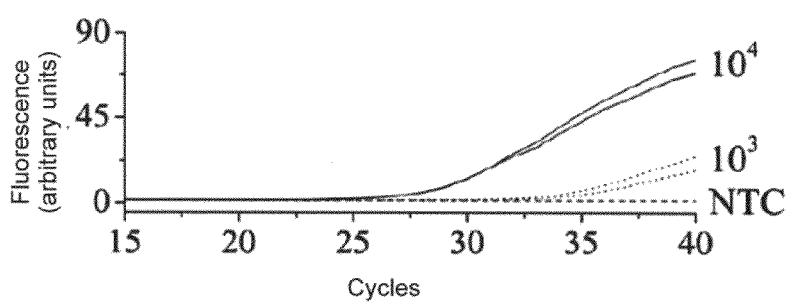
Figure 10C:
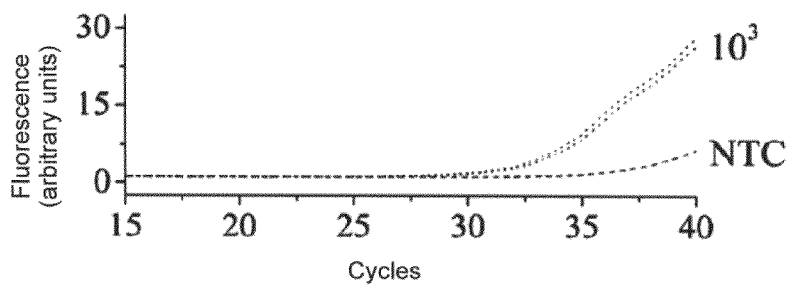
Figure 11A:
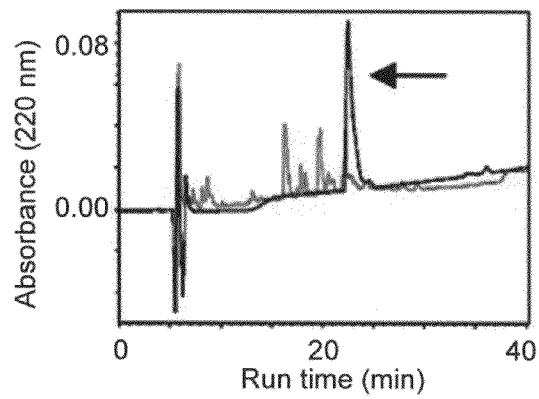
FIGS. 11A-C presents chromatograms obtained for polymers which were subjected to 10 cycles of bacterial binding and release, showing the HPLC chromatogram obtained for $K_{15}NH_2$ before (marked in black in FIG. 11A) and after (marked in red in FIG. 11A) the repetitive cycles, the HPLC chromatogram obtained for $K(NC_{12}K)_7NH_2$ before (marked in black in FIG. 11B) and after (marked in red in FIG. 11B) the repetitive cycles, and the MS spectrum with peaks for z=3, 4 and 5 (FIG. 11C) before (marked in black) and after (marked red) the repetitive cycles (arrows indicating the experimental elution time of the polymers and the fraction which was subjected to the MS analysis).
Figure 11B:
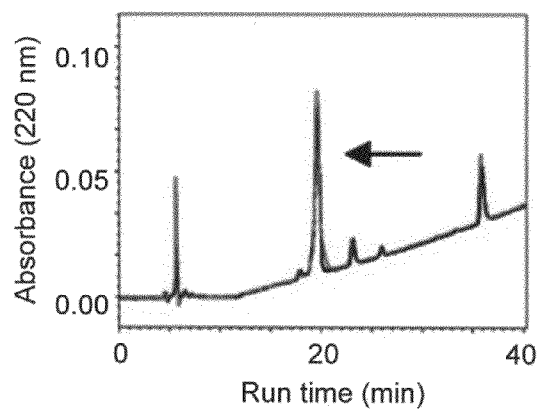
Figure 11C:
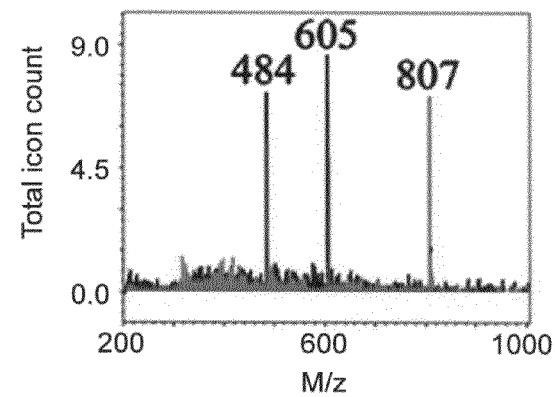

FIG. 10 presents the results of the real-time PCR amplification used for the detection of *V. cholerae* in tap water inoculated with $10^2$-$10^4$ *V. cholerae* O1 cells after its concentration using a column packed with polymer-bound beads at similar experimental conditions as described in FIG. 9, showing the relative SYBR Green fluorescence development obtained for 1 liter tap water as a function of the number of cycles of sample amplification using ompW (FIG. 10A) and ctx (FIG. 10B) locus primers, and the results obtained for a 10 liters tap water sample inoculated with $10^3$ *V. cholerae* O1 cells (10 CFU/100 ml) and amplified with ctx locus primers (FIG. 10C), and using an NTC primer as a non template control.

As can be seen in FIGS. 10A and 10B, positive identification could be achieved with a concentration as low as 100 CFU/100 ml and even lower when using *V. cholera* specific primers ompW.

Larger volumes of up to 10 liters of contaminated tap water were passed through the polymer-packed column and the eluent was tested with Real-Time PCR using primers for the ctx gene. As can be seen in FIG. 10C, positive identification could be achieved with a concentration as low as 10 CFU/100 ml. It is noted herein that five filters were needed to filter 100 ml tap water because of particle clotting, which occurred after each 20 ml per filter, in average (data not shown) whereas more than 10 liters of the same tap water could be passed through a column packed with 10 mg of polymer while capturing flowing-through bacteria.

Regeneration of Polymer-Loaded Beads:

To verify their stability and the regeneration thereof, polymer-loaded resin beads were submitted to multiple cycles of bacterial binding followed by their release with 70% ethanol. To assess the potential polymer degradation, the polymer was cleaved from the resin, analyzed by HPLC and identified by mass spectrometry.

Polymer-loaded beads were exposed to 10 consecutive cycles of bacterial binding and release with 70% ethanol, and were submitted to a cleavage reaction. The cleaved polymers were analyzed by HPLC and mass spectrometry before and after the repetitive cycles. The HPLC chromatograms were obtained over 18-minutes elution using a 1% gradient of acetonitrile in water (30% to 60%), and the fraction containing the polymer was subjected to mass spectrometry analysis.

FIG. 11 presents chromatograms obtained for polymers which were subjected to 10 cycles of bacterial binding and release, showing the HPLC chromatogram obtained for $K_{15}NH_2$ before (marked in black in FIG. 11A) and after (marked in red in FIG. 11A) the repetitive cycles, the HPLC chromatogram obtained for $K(NC_{12}K)_7NH_2$ before (marked in black in FIG. 11B) and after (marked in red in FIG. 11B) the repetitive cycles, and the MS spectrum with peaks for z=3, 4 and 5 (FIG. 11C) before (marked in black) and after (marked red) the repetitive cycles (arrows indicating the experimental elution time of the polymers and the fraction which was subjected to the MS analysis).

As can be seen in FIG. 11, unlike polylysine $K_{15}NH_2$ which deteriorated over time (see, FIG. 11A) the polymer $K(NC_{12}K)_7NH_2$ demonstrated durability and remained unchanged as assessed by the lack of chemical modifications and stability of the polymer after repeated use thereof, and confirming the polymer's chemical stability and the superior robustness of the resin-linked bacterial-capturing polymer system.

Discussion

The Examples presented hereinabove demonstrate that the polymers according to embodiments of the present invention, are able, upon conjugation to the surface of a solid support, to capture bacteria efficiently without inducing bacterial cell death. With respect to the polymer's mode of bacterial-binding action, the fact that bacteria remained viable (alive) after interacting with the support-bound polymer is noteworthy as it demonstrates that the polymer's interaction with external components of the bacterial cell wall is insufficient for inducing cytotoxicity and cell death. This finding is consistent with the assumption that the bactericidal activity of similar antimicrobial polymers requires the interaction between the free polymer, the cell membrane and/or some essential cytoplasm components [15-20]. Interestingly, various resin-linked antimicrobial peptides were shown previously to maintain bactericidal activity as the immobilized peptides typically reduced the number of viable cells by more than 5 log units [2] unlike the findings presented herein using the resin-linked polymers.

The Examples presented hereinabove also demonstrate that a bacteria-capturing polymer-based system according to some embodiments of the present invention can be used as an efficient device for capturing bacterial species while maintaining their viability under stationary as well as continuous flow conditions.

Thus, with respect to the need for new methods for efficient concentration, detection, quantification and identification of pathogens in large volumes of liquid samples, polymer-based systems according to some embodiments presented herein present several advantages, such as specificity towards microbial species which allows separating and concentrating bacteria from other contaminants with similar sizes, while avoiding system blockage and/or inhibition of the end point detection systems such as a PCR process.

Consistent with high binding affinity, bacterial capture by support-linked polymers, such as polyethylene/polystyrene support in resin beads and carboxymethyl cellulose support in biosensor chips, was found to occur rapidly, yet the bound bacteria could be readily eluted in a viable state. Such attributes might be exploited to endow flexibility for multiple filtrations and recycling. The fact that polymer binding capacity was not altered and the polymer did not undergo chemical modifications when submitted to multiple cycles of bacterial binding and release supports this concept.

Polymers can be linked to various surfaces and applied for filtration of microorganisms from various liquid media including water, food and body fluids. Furthermore, optimized polymer sequences might enable improved binding affinity and microbial selectivity.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES CITED BY NUMERALS

Other References are Cited in the Text

1. Stratmann, J., et al., *Development of a peptide-mediated capture PCR for detection of Mycobacterium avium subsp. paratuberculosis in milk.* J Clin Microbiol, 2002. 40(11): p. 4244-50.
2. Haynie, S. L., G. A. Crum, and B. A. Doele, *Antimicrobial activities of amphiphilic peptides covalently bonded to a water-insoluble resin.* Antimicrob Agents Chemother, 1995. 39(2): p. 301-7.
3. Gregory, K. and C. M. Mello, *Immobilization of Escherichia coli cells by use of the antimicrobial peptide cecropin P1.* Appl Environ Microbiol, 2005. 71(3): p. 1130-4.
4. Kulagina, N. V., et al., *Antimicrobial peptides for detection of bacteria in biosensor assays.* Anal Chem, 2005. 77(19): p. 6504-8.
5. Mor, A. and I. Radzishevsky, *Novel antimicrobial agents.* 2006: US. p. 1-41.
6. Fields, G. B. and R. L. Noble, *Solid phase peptide synthesis utilizing 9-fluorenylmethoxycarbonyl amino acids.* Int J Pept Protein Res, 1990. 35(3): p. 161-214.
7. Kustanovich, I., et al., *Structural requirements for potent versus selective cytotoxicity for antimicrobial dermaseptin S4 derivatives.* J Biol Chem, 2002. 277(19): p. 16941-51.
8. Watnick, P. I., K. J. Fullner, and R. Kolter, *A role for the mannose-sensitive hemagglutinin in biofilm formation by Vibrio cholerae El Tor.* J Bacteriol, 1999. 181(11): p. 3606-9.
9. Radzishevsky, I. S., et al., *Improved antimicrobial peptides based on acyl-lysine oligomers.* Nat Biotechnol, 2007. 25(6): p. 657-9.
10. Gaidukov, L., A. Fish, and A. Mor, *Analysis of membrane-binding properties of dermaseptin analogues: relationships between binding and cytotoxicity.* Biochemistry, 2003. 42(44): p. 12866-74.
11. Nandi, B., et al., *Rapid method for species-specific identification of Vibrio cholerae using primers targeted to the gene of outer membrane protein OmpW.* J Clin Microbiol, 2000. 38(11): p. 4145-51.
12. Shirai, H., et al., *Polymerase chain reaction for detection of the cholera enterotoxin operon of Vibrio cholerae.* J Clin Microbiol, 1991. 29(11): p. 2517-21.
13. Mor, A. and I. Radzishevsky, *Novel antimicrobial agents.* 2007: US. p. 1-53.
14. Rotem, S., I. Radzishevsky, and A. Mor, *Physicochemical properties that enhance discriminative antibacterial activity of short dermaseptin derivatives.* Antimicrob Agents Chemother, 2006. 50(8): p. 2666-72.
15. Friedrich, C. L., et al., *Antibacterial action of structurally diverse cationic peptides on gram positive bacteria.* Antimicrob Agents Chemother, 2000. 44(8): p. 2086-92.
16. Friedrich, C. L., et al., *Structure and mechanism of action of an indolicidin peptide derivative with improved activity against gram positive bacteria.* J Biol Chem, 2001. 276 (26): p. 24015-22.
17. Hancock, R. E. and D. S. Chapple, *Peptide antibiotics.* Antimicrob Agents Chemother, 1999. 43(6): p. 1317-23.
18. Huang, H. W., *Action of antimicrobial peptides: two-state model.* Biochemistry, 2000. 39(29): p. 8347-52.
19. Matsuzaki, K., *Magainins as paradigm for the mode of action of pore forming polypeptides.* Biochim Biophys Acta, 1998. 1376(3): p. 391-400.
20. Otvos, L., Jr., et al., *Interaction between heat shock proteins and antimicrobial peptides.* Biochemistry, 2000. 39(46): p. 14150-9.

---

What is claimed is:

1. A method of concentrating viable microorganisms in an aqueous solution, comprising contacting the solution with a water-insoluble matrix having a polymer capable of binding the microorganism covalently attached thereto via a C-terminus thereof, said polymer comprises a plurality of residues, wherein said plurality of residues comprises a plurality of amino acid residues and 3, 4, 5, 6, 7 or 8 ω-amino-fatty acid residues each being independently selected from the 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid, whereas each of said ω-amino-fatty acid residues is being covalently linked to at least two amino acid residues in said plurality of amino acid residues via an amine group of one amino acid residue and via a carboxyl of the other amino acid residue in said at least two amino acid residues, said polymer being selected from the group consisting of a linear polymer and a cyclic polymer, thereby binding the microorganisms to said polymer on said matrix and concentrating the microorganisms in the aqueous solution, wherein said binding is effected while maintaining viability of the microorganisms.

2. The method of claim 1, wherein each of said ω-amino-fatty acid residues is linked to each of said at least two amino acid residues via a peptide bond.

3. The method of claim 1, wherein said plurality of amino acid residues substantially consists of positively charged amino acid residues.

4. The method of claim 1, further comprising collecting said microorganisms following said binding.

5. The method of claim 1, further comprising, subsequent to said contacting, releasing the microorganisms from said matrix.

6. The method of claim 1, wherein said polymer is having the formula:

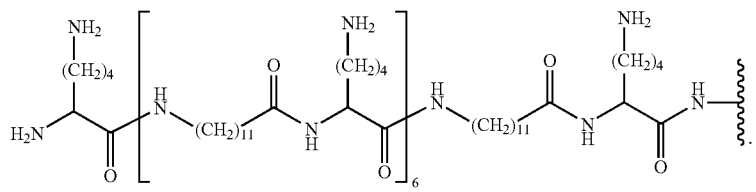

7. A method of depleting microorganisms from an aqueous solution, the method comprising:
(a) contacting the solution with a water-insoluble matrix having a polymer capable of binding the microorganism covalently attached thereto via a C-terminus thereof, wherein said polymer comprises a plurality of residues, and wherein said plurality of residues comprises a plurality of amino acid residues and 3, 4, 5, 6, 7 or 8 ω-amino-fatty acid residues each being independently selected from the group consisting of 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid, whereas each of said ω-amino-fatty acid residues is being covalently linked to at least two amino acid residues in said plurality of amino acid residues via an amine group of one amino acid residue and via a carboxyl of the other amino acid residue in said at least two amino acid residues, said polymer being selected from the group consisting of a linear polymer and a cyclic polymer, thereby binding the microorganisms to said polymer on said matrix, wherein said binding is effected while maintaining viability of the microorganisms; and subsequently
(b) collecting the solution depleted from the microorganisms.

8. The method of claim 7, wherein each of said ω-amino-fatty acid residues is linked to each of said at least two amino acid residues via a peptide bond.

9. The method of claim 7, wherein said plurality of amino acid residues substantially consists of positively charged amino acid residues.

10. The method of claim 7, further comprising, subsequent to said contacting, releasing the microorganisms from said matrix.

11. The method of claim 7, wherein said polymer is having the formula:

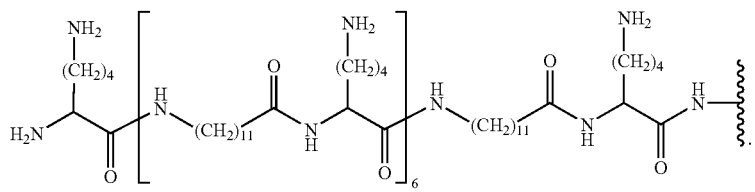

12. A device for concentrating microorganisms while maintaining viability of the microorganisms, the device comprising at least one casing and a water-insoluble matrix embedded therein, said water insoluble matrix having a polymer capable of binding the microorganism covalently attached thereto via a C-terminus thereof, said polymer comprises a plurality of residues, wherein said plurality of residues comprises a plurality of amino acid residues and 3, 4, 5, 6, 7 or 8 ω-amino-fatty acid residues each being independently selected from the group consisting of 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid, whereas each of said ω-amino-fatty acid residues is covalently linked to at least two amino acid residues in said plurality of amino acid residues via an amine group of one amino acid residue and via a carboxyl of the other amino acid residue in said at least two amino acid residues, said polymer being selected from the group consisting of a linear polymer and a cyclic polymer, wherein said matrix is configured to allow an aqueous solution which comprises the microorganism to flow through, thereby binding the microorganisms to said polymer on said matrix, wherein said binding is effected while maintaining viability of the microorganisms.

13. The device of claim 12, wherein each of said ω-amino-fatty acid residues is linked to each of said at least two amino acid residues via a peptide bond.

14. The device of claim 12, wherein said plurality of amino acid residues substantially consists of positively charged amino acid residues.

15. The device of claim 12, wherein said polymer is having the formula:

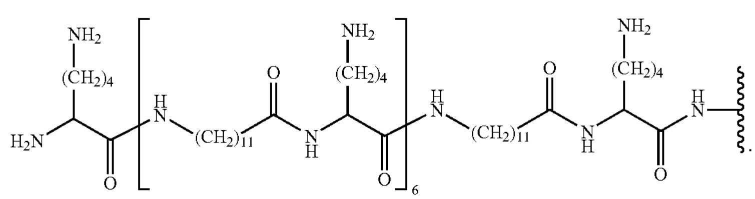

16. A method for detection and identification of viable microorganisms in an aqueous solution comprising:

(a) contacting the solution with a water-insoluble matrix having a polymer capable of binding the microorganism covalently attached thereto via a C-terminus thereof, said polymer comprises a plurality of residues, wherein said plurality of residues comprises a plurality of amino acid residues and 3, 4, 5, 6, 7 or 8 ω-amino-fatty acid residues each being independently selected from the group consisting of 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid, whereas each of said ω-amino-fatty acid residues is being covalently linked to at least two amino acid residues in said plurality of amino acid residues via an amine group of one amino acid residue and via a carboxyl of the other amino acid residue in said at least two amino acid residues, said polymer being selected from the group consisting of a linear polymer and a cyclic polymer, thereby binding the microorganisms to said polymer on said matrix, wherein said binding is effected while maintaining viability of the microorganisms; and (b) identifying the microorganism bound to said matrix.

17. The method of claim 16, wherein each of said ω-amino-fatty acid residues is linked to each of said at least two amino acid residues via a peptide bond.

18. The method of claim 16, wherein said plurality of amino acid residues substantially consists of positively charged amino acid residues.

19. The method of claim 16, wherein said polymer is having the formula:

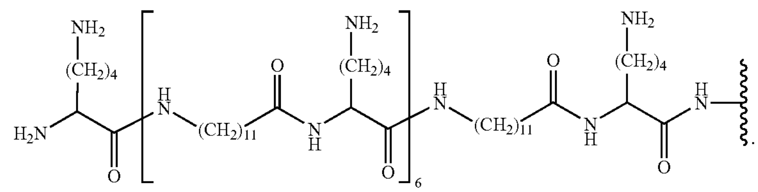

20. The method of claim 16, wherein the detection and identification of microorganisms is quantitative.

21. The method of claim 16, further comprising, prior to said identifying, isolating the microorganisms from the matrix.

22. A sterile composition comprising a water-insoluble matrix having a polymer covalently attached via a C-terminus thereof to said matrix, said polymer comprising a plurality of residues, wherein said plurality of residues comprises a plurality of amino acid residues and 3, 4, 5, 6, 7 or 8 ω-amino-fatty acid residues each being independently selected from the group consisting of 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid, whereas each of said ω-amino-fatty acid residues is being covalently linked to at least two amino acid residues in said plurality of amino acid residues via an amine group of one amino acid residue and via a carboxyl of the other amino acid residue in said at least two amino acid residues, said polymer being selected from the group consisting of a linear polymer and a cyclic polymer, wherein said polymer is being capable of binding a microorganism and the composition is being identified for binding said microorganism to said polymer while maintaining viability of said microorganism.

23. The composition of claim 22, wherein each of said ω-amino-fatty acid residue is linked to each of said at least two amino acid residues via a peptide bond.

24. The composition of claim 22, wherein said plurality of amino acid residues substantially consists of positively charged amino acid residues.

25. A composition comprising a water-insoluble matrix having a polymer capable of binding a microorganism covalently attached thereto via a C-terminus thereof and further comprising microorganisms bound to said polymer, wherein said microorganisms are biologically viable, said polymer comprising a plurality of residues, wherein said plurality of residues comprises a plurality of amino acid residues and 3, 4, 5, 6, 7 or 8 ω-amino-fatty acid residues each being independently selected from the group consisting of 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid, whereas each of said ω-amino-fatty acid residues is being covalently linked to at least two amino acid residues in said plurality of amino acid residues via an amine group of one amino acid residue and via a carboxyl of the other amino acid residue in said at least two amino acid residues, said polymer being selected from the group consisting of a linear polymer and a cyclic polymer.

26. The method of claim 1, wherein the aqueous solution is a bodily fluid.

27. The method of claim 26, wherein said bodily fluid is a blood sample.

28. The method of claim 7, wherein the aqueous solution is a bodily fluid.

29. The method of claim 28, wherein said bodily fluid is a blood sample.

30. The device of claim 12, wherein said aqueous solution is a bodily fluid.

31. The method of claim 30, wherein said bodily fluid is a blood sample.

32. The method of claim 16, wherein the aqueous solution is a bodily fluid.

33. The method of claim 32, wherein said bodily fluid is a blood sample.

34. The device of claim 12, wherein said plurality of residues comprises 5, 6, 7 or 8 hydrophobic moiety residues.

35. The composition of claim 22, wherein said plurality of residues comprises 5, 6, 7 or 8 hydrophobic moiety residues.

36. The composition of claim 25, wherein said plurality of residues comprises 5, 6, 7 or 8 hydrophobic moiety residues.

37. The method of claim 1, wherein said plurality of residues comprises 5, 6, 7 or 8 hydrophobic moiety residues.

38. The method of claim 7, wherein said plurality of residues comprises 5, 6, 7 or 8 hydrophobic moiety residues.

39. The method of claim 16, wherein said plurality of residues comprises 5, 6, 7 or 8 hydrophobic moiety residues.

\* \* \* \* \*

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 1
aggattagat accctggtag t                                              21

<210> SEQ ID NO 2
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 2
cgaattaaac cacatgctcc a                                              21

<210> SEQ ID NO 3
<211> LENGTH: 24
<212> TYPE: DNA
<213> ORGANISM: Artificial sequence
<220> FEATURE:
<223> OTHER INFORMATION: Single strand DNA oligonucleotide
```

-continued

```
<400> SEQUENCE: 3
caccaagaag gtgactttat tgtg                                              24

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
ggaaagtcga attagcttca cc                                                22

<210> SEQ ID NO 5
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 5
ctcagacggg atttgttagg cacg                                              24

<210> SEQ ID NO 6
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 6
tctatctctg tagcccctat tacg                                              24

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
ggagataatt gagacagttc ag                                                22

<210> SEQ ID NO 8
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 8
atgtcccagg tgacgatg                                                     18
```